US011883128B2

(12) United States Patent
Cross et al.

(10) Patent No.: US 11,883,128 B2
(45) Date of Patent: Jan. 30, 2024

(54) MULTISPECTRAL MOBILE TISSUE ASSESSMENT

(71) Applicant: MIMOSA DIAGNOSTICS INC., Toronto (CA)

(72) Inventors: Karen Michelle Cross, Toronto (CA); General Leung, Toronto (CA)

(73) Assignee: MIMOSA DIAGNOSTICS INC., Toronto (CA)

(*) Notice: Subject to any disclaimer, the term of this patent is extended or adjusted under 35 U.S.C. 154(b) by 1315 days.

(21) Appl. No.: 16/327,786

(22) PCT Filed: Aug. 24, 2017

(86) PCT No.: PCT/CA2017/050998
§ 371 (c)(1),
(2) Date: Feb. 22, 2019

(87) PCT Pub. No.: WO2018/035612
PCT Pub. Date: Mar. 1, 2018

(65) Prior Publication Data
US 2019/0216326 A1 Jul. 18, 2019

Related U.S. Application Data

(60) Provisional application No. 62/378,939, filed on Aug. 24, 2016.

(51) Int. Cl.
*A61B 5/00* (2006.01)
*G03B 15/03* (2021.01)
(Continued)

(52) U.S. Cl.
CPC ............ *A61B 5/0075* (2013.01); *A61B 5/004* (2013.01); *A61B 5/14542* (2013.01);
(Continued)

(58) Field of Classification Search
CPC ... A61B 5/0075; A61B 5/004; A61B 5/14542; A61B 5/14552; A61B 5/445;
(Continued)

(56) References Cited

U.S. PATENT DOCUMENTS 5,929,985 A 7/1999 Sandison et al.
6,640,130 B1 10/2003 Freeman et al.
(Continued)

FOREIGN PATENT DOCUMENTS

WO 2001001854 A2 1/2001
WO 2001003050 A1 1/2001
(Continued)

OTHER PUBLICATIONS

Zuzak, K. J. et al. "Noninvasive Determination of Spatially Resolved and Time-Resolved Tissue Perfusion in Humans During Nitric Oxide Inhibition and Inhalation by Use of a Visible-Reflectance Hyperspectral Imaging Technique", Published in Circulation 104(24):2905-10, Dec. 2001 (6 pages) http://www.circulationaha.org.
(Continued)

Primary Examiner — Peter Luong
(74) Attorney, Agent, or Firm — BERESKIN & PARR LLP/ S.E.N.C.R.L. s.r.l; Tonino Rosario Orsi

(57) ABSTRACT

A method for performing remote tissue assessment of a tissue region includes selecting imaging parameters, obtaining M image datasets of the tissue region when the tissue region is illuminated by a light signal having a unique discrete wavelength, obtaining a reference image dataset of the tissue region without illumination, processing the M+1 image datasets to obtain M marker maps where each marker map corresponds to a different physiological marker, and analyzing at least one of the marker maps to determine whether a physiological condition exists at the tissue region
(Continued)

or to monitor the status of an existing physiological condition at the tissue region. In one or more embodiments, the method may be performed by a portable light source unit including a housing configured for use with a mobile device having a camera, or by a system including a light source unit, an optical sensor module, and a mobile device.

25 Claims, 10 Drawing Sheets

(51) Int. Cl.
  *G03B 29/00* (2021.01)
  *A61B 5/145* (2006.01)
  *A61B 5/1455* (2006.01)
  *A61B 90/30* (2016.01)
  *A61B 90/00* (2016.01)

(52) U.S. Cl.
  CPC ......... *A61B 5/14552* (2013.01); *A61B 5/445* (2013.01); *A61B 5/447* (2013.01); *A61B 90/00* (2016.02); *A61B 90/30* (2016.02); *A61B 90/361* (2016.02); *G03B 15/03* (2013.01); *G03B 29/00* (2013.01); *G03B 2206/00* (2013.01); *G03B 2215/0514* (2013.01)

(58) Field of Classification Search
  CPC ......... A61B 5/447; A61B 90/00; A61B 90/30; A61B 90/361; G03B 15/03; G03B 29/00; G03B 2206/00; G03B 2215/0514
  See application file for complete search history.

(56) References Cited

U.S. PATENT DOCUMENTS

| | | | |
|---|---|---|---|
| 6,810,279 | B2 | 10/2004 | Mansfield et al. |
| 7,729,747 | B2 | 6/2010 | Stranc et al. |
| 7,860,554 | B2 | 12/2010 | Leonardi et al. |
| 3,060,188 | A1 | 11/2011 | Stranc et al. |
| 8,175,688 | B2 | 5/2012 | Lewis et al. |
| 8,224,425 | B2 | 7/2012 | Freeman et al. |
| 8,320,996 | B2 | 11/2012 | Panasyuk et al. |
| 8,374,682 | B2 | 2/2013 | Freeman et al. |
| 8,792,098 | B2 | 7/2014 | Dewald et al. |
| 8,892,192 | B2 | 11/2014 | Cuccia et al. |
| 8,971,984 | B2 | 3/2015 | Freeman et al. |
| 9,480,424 | B2 | 11/2016 | Darty et al. |
| 9,526,427 | B2 | 12/2016 | Darty et al. |
| 9,968,285 | B2 | 5/2018 | Valsan et al. |
| 10,278,636 | B2 | 5/2019 | Wu et al. |
| 11,266,345 | B2 | 3/2022 | Saiko et al. |
| 2014/0293091 | A1 | 10/2014 | Rhoads et al. |
| 2015/0051498 | A1 | 2/2015 | Darty |
| 2015/0148636 | A1* | 5/2015 | Benaron ............ A61B 5/02405 600/328 |
| 2015/0271380 | A1 | 9/2015 | Darty et al. |
| 2016/0157725 | A1 | 6/2016 | Munoz |
| 2017/0124709 | A1 | 5/2017 | Rithe et al. |
| 2018/0106676 | A1 | 4/2018 | Jang et al. |
| 2018/0160953 | A1 | 6/2018 | Valsan et al. |
| 2018/0198993 | A1 | 7/2018 | Barnes et al. |
| 2018/0328855 | A1 | 11/2018 | Kido |
| 2019/0090751 | A1 | 3/2019 | Iwang et al. |

FOREIGN PATENT DOCUMENTS

| | | |
|---|---|---|
| WO | 2007022508 A2 | 2/2007 |
| WO | 2009117603 A2 | 9/2009 |
| WO | 2010019515 A2 | 2/2010 |
| WO | 2011113162 A1 | 9/2011 |
| WO | 2014007869 A2 | 1/2014 |
| WO | 2016094521 A1 | 6/2016 |
| WO | 2018160963 A1 | 9/2018 |
| WO | 2018211482 A1 | 11/2018 |
| WO | 2019003245 A1 | 1/2019 |
| WO | 2019054958 A2 | 3/2019 |

OTHER PUBLICATIONS

International Preliminary Report on Patentability in corresponding international Application No. PCT/CA2017/050998 dated Mar. 7, 2019 (9 pages).
Anuradha Godavarty, "A near-IR optical scanner to detect wound healing", SPIE, 2015, https://spie.org/news/5975-a-near-ir-optical-scanner-to-detect-wound-healing?SSO=1.
Anuradha Godavarty et al. "Diabetic Wound Imaging Using a Noncontact Near-Infrared Scanner: A Pilot Study", Journal of Diabetes Science and Technology 2015, vol. 9(5) pp. 1158-1159.
Nirmal Keshava, A Survey of Spectral Unmixing Algorithms, Lincoln Laboratory Journal, vol. 14, No. 1, 2003.
Matthew Livingston, "Multispectral Oximetry Imaging Readings with Associated Healing Trajectory", Kent Multispectral Imaging, Kent Imaging Inc., Calgary, Alberta downloaded on Aug. 19, 2016.
Parra L., et al., "Unmixing hyperspectral data", Advances in neural information processing systems, 12. 1999.
Portilla Rodriguez, M et al., "NIR camera for early detection of diabetic ulcers" (2014). Focus on Creative Inquiry. Paper 46. http://tigerprints.clemson.edu/foci/46.
Dmitry Yudovsky et al., "Hyperspectral Imaging in Diabetic Foot Wound Care", Journal of Diabetes Science and Technology, vol. 4, Issue 5, Sep. 2010, Diabetes Technology Society, pp. 1099-1113.
Exam Report issued in corresponding Australian application No. AU2017315334 dated Sep. 20, 2021 (4 pages).
Partial European Search Report issued in corresponding EP publication No. EP3504590 dated Feb. 26, 2020 (1 page).
International Search Report issued in corresponding application No. PCT/CA2017/050998 dated Nov. 23, 2017 (5 pages).
Written Opinion of the International Searching Authority issued in corresponding application No. PCT/CA2017/050998 dated Nov. 23, 2017 (7 pages).

* cited by examiner

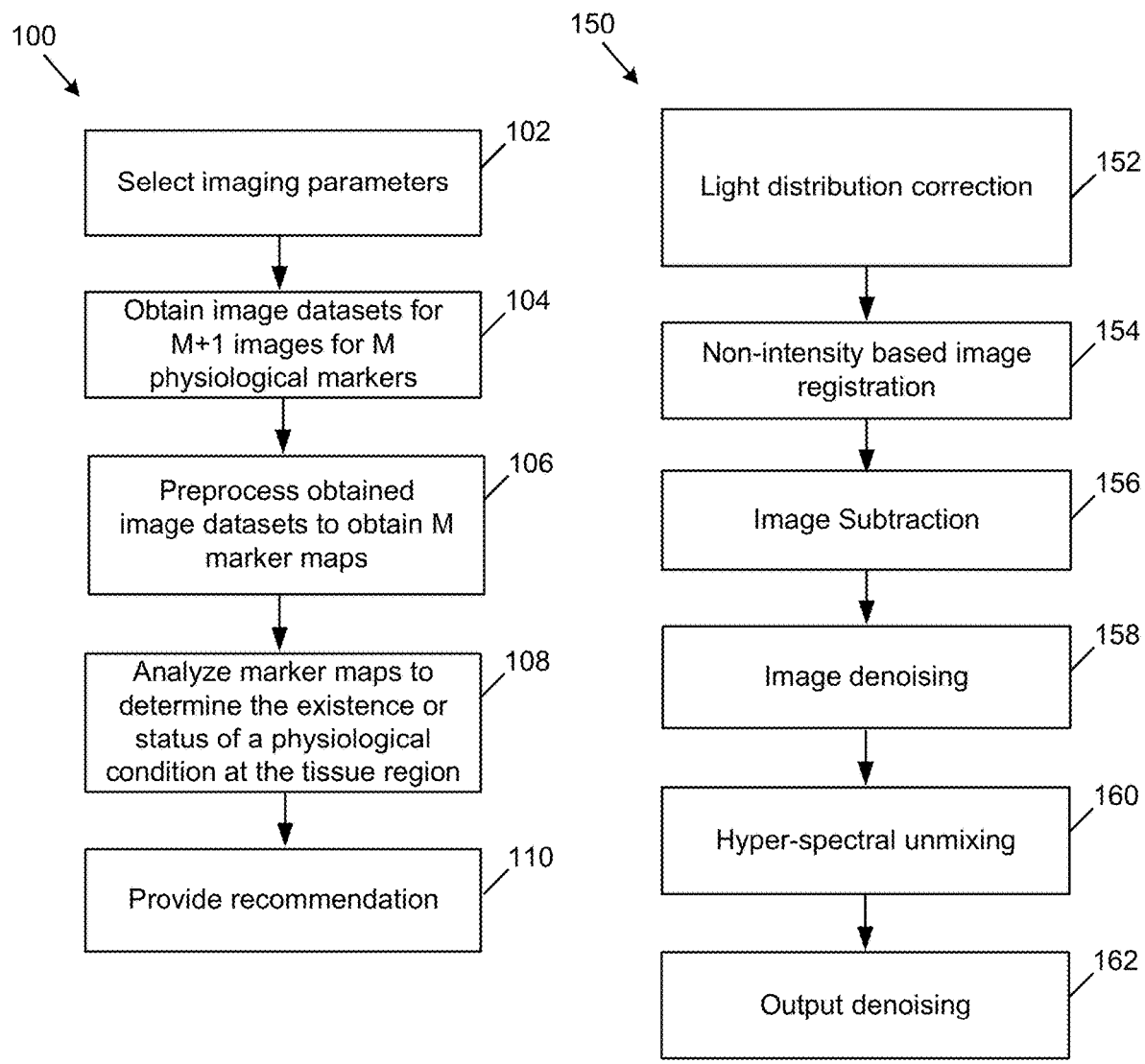

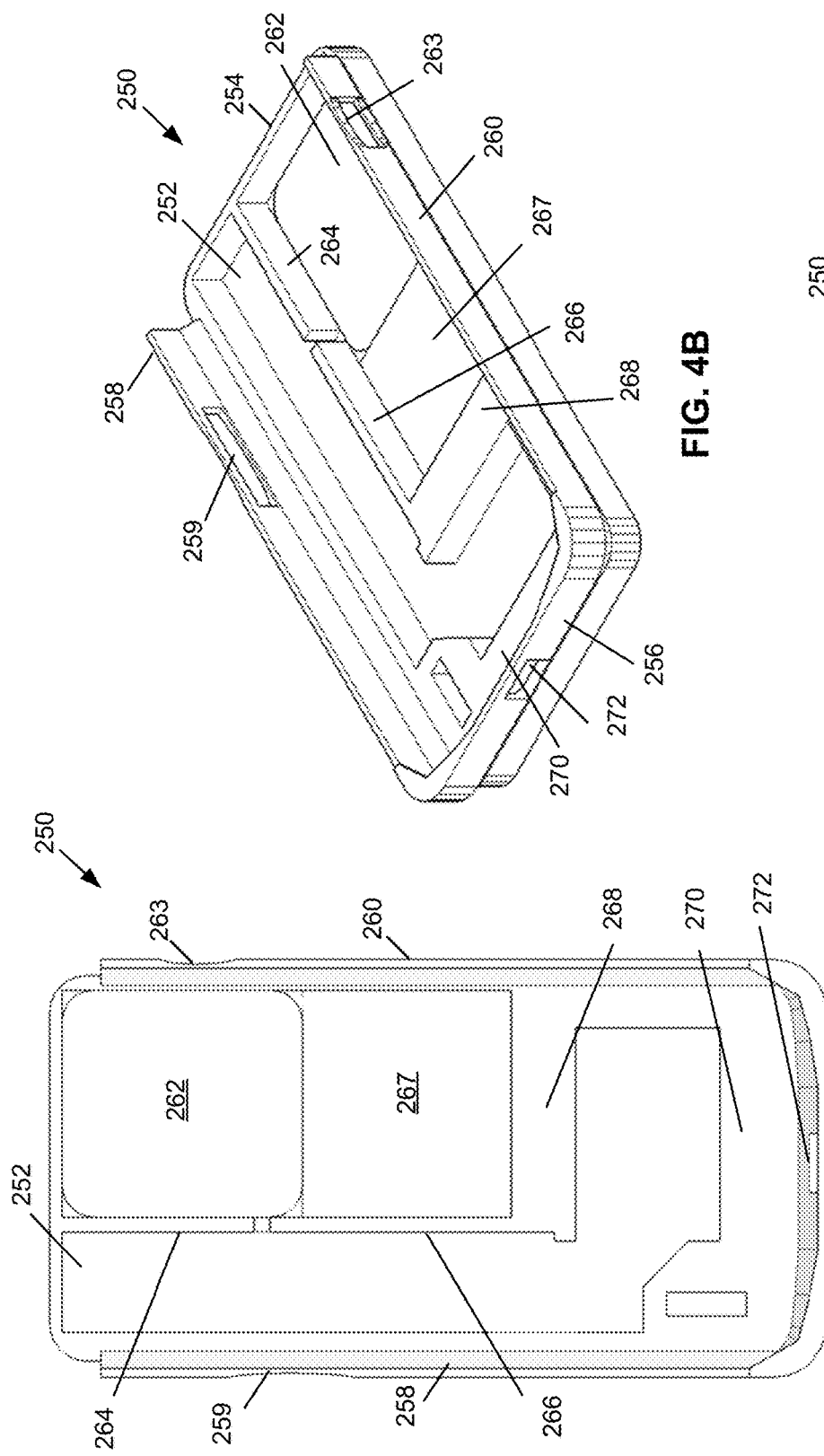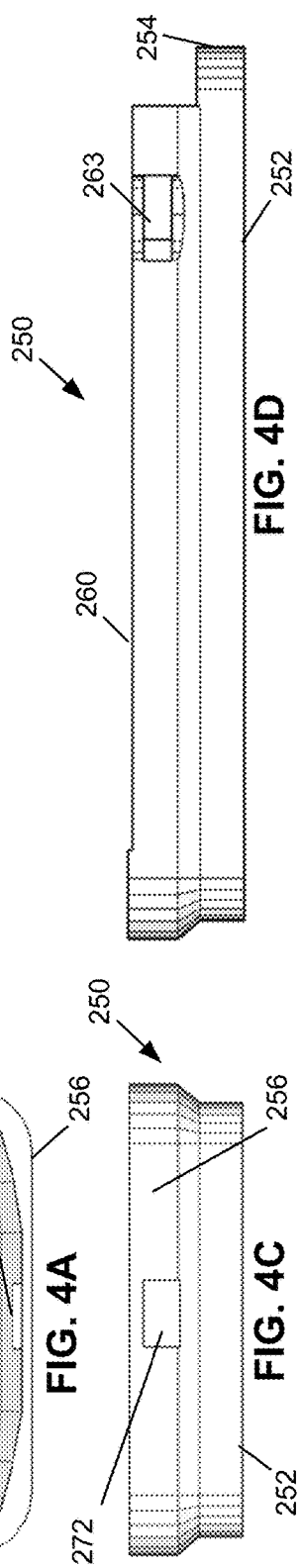

MULTISPECTRAL MOBILE TISSUE ASSESSMENT

FIELD

Various embodiments are described herein for a device, method and system allowing for the remote assessment of a tissue region.

BACKGROUND

Patients with diabetes are 20 times more likely to have a lower limb amputation than the general population. This amputation rate can be increased by 50% if the patient has a Diabetic Foot Ulcer (DFU). Surgical limb salvage is only possible if the patient presents before irreversible tissue damage. However, there are currently no non-invasive tools that can give an early warning about the tissue health of diabetic legs and feet. This means that patients come to the hospital in many cases too late to save their foot or toes. If there were an early warning tool, it might be possible to detect the disease earlier, intervene earlier, save more limbs, and improve these patient's lives.

This is important since diabetic patients are 20 times more likely to be hospitalized with a non-traumatic lower limb amputation. The presence of a diabetic foot ulcer (DFU) increases the risk of amputation by 50%. These patients typically present with micro-angiopathic disease, extensive arterial calcification and concomitant large vessel peripheral vascular disease. These features lead to chronic ischemia of the lower extremities precluding these patients to limb ulceration. In addition, patients with diabetes have peripheral neuropathy which means they lack sensation in their feet and cannot protect themselves from injury. For example, a tight fitting shoe causing a blister or pressure from stepping on a rough or sharp object is not felt by the patient and leads to small abrasions to the skin which eventually can progress to DFU's.

Early diagnosis and management of DFUs can mean the difference between life and death for diabetic patients. The one year mortality rate is 30% for diabetics whom require lower extremity amputation. This is more than the lifetime risk of dying from cancers of the breast and colon. The 5 year mortality rate post amputation in patients with diabetes is 70%. Approximately, 85% of patients in the hospital with concomitant lower extremity amputations have diabetes. There are currently no non-invasive techniques for monitoring the tissue health of the lower extremity. Personal glucometers revolutionized diabetes care 50 years ago by permitting "at home" monitoring of blood glucose and being able to have closer glycemic control. A personal diagnostic device for "foot health" monitoring may have the same impact on the incidence of DFU and DFU-related amputations through early recognition and intervention.

SUMMARY OF VARIOUS EMBODIMENTS

In a broad aspect, at least one embodiment described herein provides a portable light source unit for illuminating a tissue region for imaging, wherein the light source unit includes a housing being configured for use with a mobile device having a camera, the housing having a base member with a first aperture and at least two opposing side walls disposed inwardly and being spaced apart to releasably receive edges of the mobile device and the first aperture having a location that is aligned with a location of the camera of the mobile device when the portable light source unit is mounted on the mobile device; a light source module disposed along a portion of the base member and oriented to generate a light signal in a common direction with the camera, the light source module being located to be outside of the field of view of the camera; and a controller that is operatively coupled with the light source module and a processor of the mobile device to generate a light control signal for controlling the light source module to generate light to illuminate the tissue region prior to the camera of the mobile device obtaining an image of the tissue region.

In at least some embodiments, the controller includes a communication unit for wirelessly communicating with the mobile device. The communication unit may include a Bluetooth radio.

In at least some embodiments, the portable light source unit further includes a power module having a battery and a voltage regulator to provide power to electronic components of the portable light source unit.

Alternatively, in at least some embodiments, the portable light source unit further is coupled to the mobile device to receive power therefrom to provide power to electronic components of the portable light source unit.

In at least some embodiments, the light source module, the controller and the power supply unit are mounted on a circuit board that is disposed within the housing.

In at least some embodiments, the light source module is configured to generate the light signal to have one of N single discrete wavelengths in the visible light and near infrared spectrum.

In at least some embodiments, the light source module includes N LED drivers and N LEDs, where each LED is configured to generate a light signal having a single discrete unique wavelength in the range of about 600 nm to 1,000 nm.

In at least some embodiments, the light source module includes a second aperture that is aligned with the camera of the mobile device when the portable light source unit is mounted on the mobile device and the LEDs are arranged in a circular pattern around the second aperture.

The N discrete wavelengths of the light source module may generally be selected based on N physiological markers of interest that are measured when the tissue region is imaged.

In another aspect, at least one embodiment described herein provides a method for performing remote tissue assessment for a tissue region, wherein the method involves: selecting imaging parameters; obtaining M image datasets of the tissue region when the tissue region is illuminated by a light signal having a unique discrete wavelength selected from M discrete unique frequencies; obtaining a reference image dataset of the tissue region when the tissue region is not illuminated; processing the M+1 image datasets to obtain M marker maps where each marker map corresponds to a different physiological marker; and analyzing at least one of the marker maps to determine whether a physiological condition exists at the tissue region or to monitor the status of an existing physiological condition at the tissue region.

In at least some embodiments, the method further involves providing a recommendation depending on the analysis results, the recommendation comprising one of performing further assessment of the tissue region and applying a type of treatment to the tissue region.

In at least some embodiments, the discrete wavelengths are selected in the range of about 600 nm to 1,000 nm. More particularly, in at least some embodiments, the discrete wavelengths include 620, 630, 700, 810, 880 and 940 nm.

In at least some embodiments, the analysis involves combining at least two of the marker maps to create a combined marker map and performing measurements on the combined marker map.

In at least some embodiments, the physiological markers for the marker maps include at least one of total hemoglobin, oxygen saturation, methemoglobin, water, and melanin.

In at least some embodiments, the marker map includes a water marker map that is used for at least one of determining end points of resuscitation, monitoring burn edema, monitoring sepsis, and monitoring infection.

In at least some embodiments, the marker map includes a water marker map that is used for at least one of skin hydration, skin dehydration, and skin moisture absorption.

In at least some embodiments, the marker map includes a melanin marker map that is used for at least one of skin pigmentation monitoring, skin whitening treatment, and treatments for skin hyperpigmentation.

In at least some embodiments, the marker map includes a collagen marker map that is used to monitoring at least one of wound healing, scar outcome and scar progression.

In at least some embodiments, the method involves generating an alert when the analysis of the at least one marker map indicates a sudden change in the physiological condition.

In at least some embodiments, the method involves determining a relationship between at least two of the marker map; and analyzing the determined relationship to determine the composition of blood oxygenation and oxidation for the tissue region.

In at least some embodiments, the processing involves performing multispectral unmixing to generate the marker maps.

In at least some embodiments, the processing involves applying at least one of light distribution correction, non-intensity based image registration, image subtraction, image denoising and output denoising to improve the signal to noise ratio of the generated marker maps.

In at least some embodiments, the method involves using a handheld portable imaging device for imaging the tissue region, the handheld portable imaging device including a light source unit for generating the light signal to illuminate the tissue region and a mobile device having a camera for obtaining the image datasets.

In at least some embodiments, the image datasets are sent from the mobile device to an analysis server which performs the processing and analysis of the image datasets.

In at least some embodiments, the mobile device performs the processing and analysis of the image datasets.

In at least some embodiments, the method includes using a system for imaging the tissue region, the system including a light source unit for generating the light signal to illuminate the tissue region, an optical sensor module in communication with the light source unit for obtaining the image datasets, and a mobile device in communication with the light source unit.

In another aspect, at least one embodiment described herein provides a system for remote tissue assessment of a tissue region, wherein the system includes: a light source unit for generating a light signal to illuminate the tissue region, the light signal having a unique discrete wavelength selected from M discrete unique frequencies; and a mobile device having a camera for obtaining M image datasets of the tissue region when the tissue region is illuminated by the light signal and obtaining a reference image dataset of the tissue region when the tissue region is not illuminated, wherein the system is configured to: process the M+1 image datasets to obtain M marker maps where each marker map corresponds to a different physiological marker; and analyze at least one of the marker maps to determine whether a physiological condition exists at the tissue region or to monitor the status of an existing physiological condition at the tissue region.

The system may further include an analysis server portal.

According to one or more embodiments, a system for remote tissue assessment of a tissue region includes a light source unit for generating a light signal to illuminate the tissue region, the light signal having a unique discrete wavelength selected from M discrete unique frequencies, an optical sensor module for obtaining M image datasets of the tissue region when the tissue region is illuminated by the light signal and obtaining a reference image dataset of the tissue region when the tissue region is not illuminated, wherein the optical sensor module is in communication with the light source unit; and a mobile device in communication with the light source unit, wherein the system is configured to process the M+1 image datasets to obtain M marker maps where each marker map corresponds to a different physiological marker, and analyze at least one of the marker maps to determine whether a physiological condition exists at the tissue region or to monitor the status of an existing physiological condition at the tissue region.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2 is a flowchart of an example embodiment of a method for remote optical tissue assessment.

FIG. 3A is a flowchart of an example embodiment of an image processing method that can be used with the method for remote optical tissue assessment shown in FIG. 2.

FIG. 4A is a plan view of an inner surface of an example embodiment of a housing for the light source unit of FIG. 1.

FIG. 4B is a perspective view of the inner surface of the housing of FIG. 4A.

FIG. 4C is a side view of the bottom edge of the housing of FIG. 4A.

FIG. 4D is a side view of the housing of the FIG. 4A.

Figure 1:
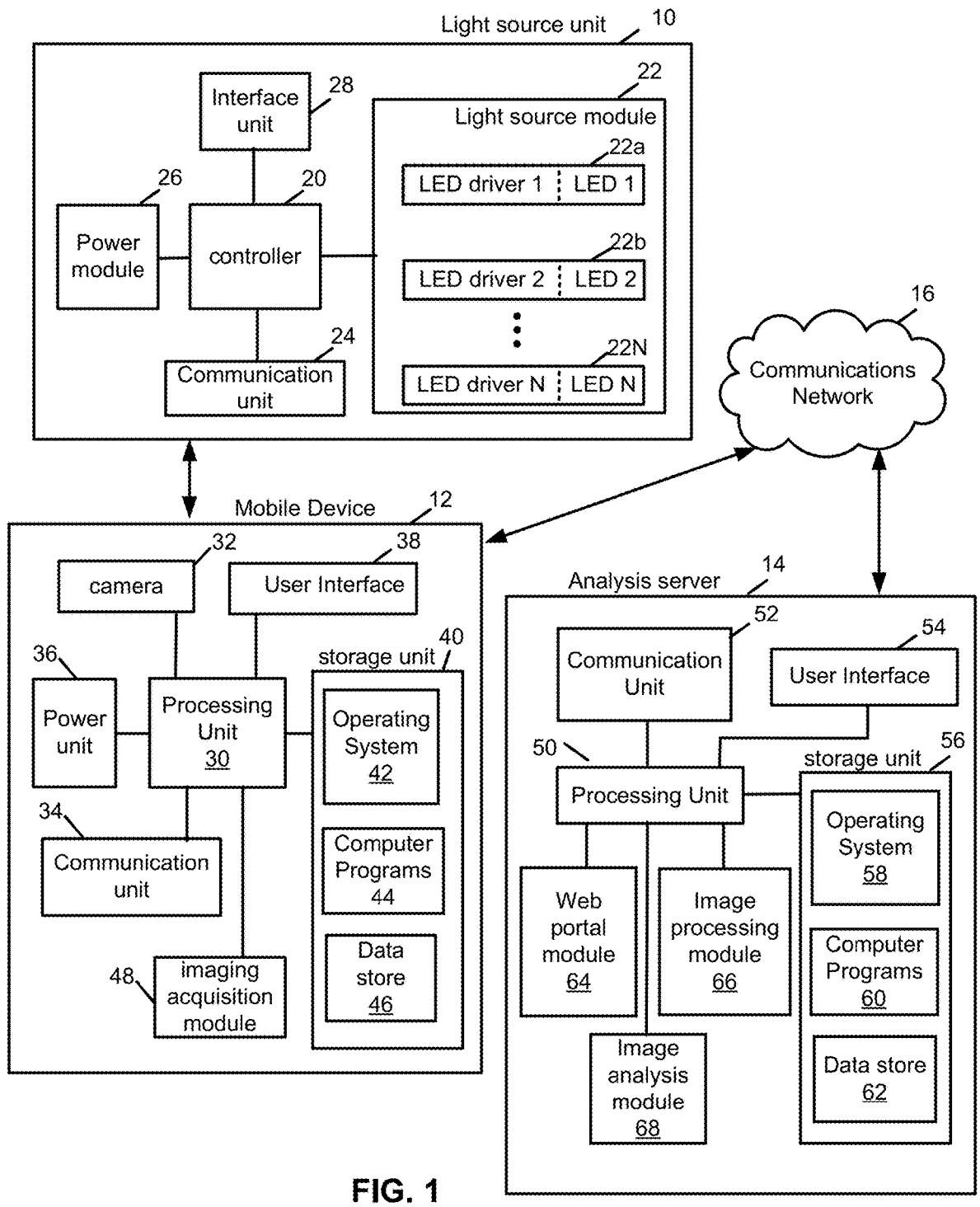
FIG. 1 is a block diagram of an example embodiment of a system including a portable imaging device having a light source unit and a mobile device for remote tissue assessment.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices and or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have an electrical connotation. For example, as used herein, the terms coupled or coupling can indicate that two elements or devices can be directly connected to one another or connected to one another through one or more intermediate elements or devices via an electrical signal that can be transmitted over a physical wire or cable or transmitted wirelessly. In other instances the terms coupled or coupling can indicate that two elements are directly mechanically connected to one another or mechanically connected to one another through another element or linkage.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 5% or 10%, for example, as the case may be.

The example embodiments of the systems and methods described in accordance with the teachings herein may be implemented as a combination of hardware or software. Accordingly, the example embodiments described herein may be implemented, at least in part, by using one or more computer programs, executing on one or more programmable devices comprising at least one processing element, and a data store (including volatile and non-volatile memory and/or storage elements). These devices may also have at least one input device (e.g. a receiver) and at least one output device (e.g. a transmitter) or in some embodiments an input/output device such as a transceiver, depending on the nature of the device. The programmable devices may include a processor, a controller, or an Application Specific Integrated Circuit (ASIC), for example. Program code can be applied to input data to perform the functions described herein and to generate output data. The output data can be supplied to one or more output devices for outputting to one or more electronic devices.

There may be some elements that are used to implement at least part of one of the embodiments described herein that may be implemented via software that is written in a high-level procedural language or object oriented programming and/or scripting language. Accordingly, the program code may be written using an event-driven paradigm with objects or any other suitable programming language and may include modules or classes, as is known to those skilled in object oriented programming. Alternatively, or in addition thereto, some of these elements implemented via software may be written in assembly language, machine language or firmware as needed. In either case, the language may be a compiled or an interpreted language.

At least some of these software programs may be stored on a storage media (e.g. a computer readable medium such as, but not limited to, ROM, FLASH memory and the like) or a device that is readable by a general or special purpose programmable device. The software program code, when read by the programmable device, configures the programmable device to operate in a new, specific and predefined manner in order to perform at least one of the methods described in accordance with the teachings herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, interne transmissions (e.g. downloads), media, digital and analog signals, and the like. The computer useable instructions may also be in various formats, including compiled and non-compiled code.

In accordance with the teachings herein, at least one example embodiment of a portable imaging device that incorporates optical components is provided herein. The portable imaging device can be used in a variety of ways. For example, the portable imaging device can be used in remote assessment of a tissue region for a physiological condition and therefore provide an early warning for the occurrence of the physiological condition or for a worsening status of the physiological condition.

The portable imaging device is hand-held and can be easily manipulated with one hand in order to obtain images for any body part. The device is also easy to use. Accordingly, the device can be used by lay people to assess tissue health at various remote locations with respect to a medical institution (e.g. a hospital, clinic or the like), such as a person's home. The portable imaging device will permit for rapid assessment of wounded tissue, non-wounded tissue and tissue health, which has been previously unavailable to clinicians and patients.

In an example embodiment, the portable imaging device may be incorporated with wound management software that implements a wound tracking system that can be used to automate follow up appointments and provide early warning for the detection of negative tissue changes thereby alerting physicians, clinicians or healthcare workers to patients requiring further assessment and intervention such as dressing, surgery and the like. This will reduce the number of hospital visits and permit early detection of tissue ischemia.

In at least one example embodiment described in accordance with the teachings herein, image data can be obtained for a sequence of images of a tissue region for a portion of a body part. The sequence of images may be obtained while illuminating a tissue region with a sequence of different wavelengths of visible and Near InfraRed (NIR) light so that each image is obtained while illuminating the tissue region with light having a different wavelength. A reference image can be obtained when the tissue region is not illuminated by light for use in accounting for and removing the inherent noise in the other images of the tissue region that were obtained during illumination. The body part can be any part of a person or an animal. For example, the body part can be, but is not limited to, a leg, a foot, a finger, or a hand. By comparing the image data for the different images obtained at different wavelengths, it may be determined how much perfusion, oxygenation and tissue injury exists in the imaged tissue. The imaged tissue can include skin, muscle, ligaments, vasculature or bones.

The imaging can be performed for a variety of conditions in which it is important to perform tissue monitoring such as, but not limited to, monitoring diabetic ulcers, for example. By early recognition and screening of diabetics, it may be possible to save limbs and lives. For example, diabetic patients have both small and large vessel peripheral vascular disease. These features can lead to chronic ischemia of the lower extremities and predispose these patients to limb ulceration. The lower extremities can be imaged using the portable imaging device to determine if a variety of physiological conditions has occurred and if so the severity of the physiological condition thereby allowing for tissue viability to be assessed. In contrast conventional monitoring techniques may be limited to monitoring for particular conditions such as the existence of ischemia or the physical measurement of a wound (and if so the severity of the ischemia).

The inventors have found that discriminating tissue from a diabetic limb ulcer from healthy viable tissue may be done by evaluating the tissue region for certain physiological markers such as, but not limited to, wound oxygenation, perfusion (i.e. total hemoglobin), methemoglobin and water content. To the best of their knowledge, the inventors are the first to use metHb as a physiological marker and also to be able to create digital images of metHb using portable optical imaging. In addition, the inventors have found that changes in certain measures of these physiological markers, when taken alone or in a certain combination, may serve as an early warning of the onset of tissue damage before the presentation of clinical symptoms or even a wound. The inventors have also found that these physiological markers can be determined by illuminating the tissue region using several different discrete wavelengths of light instead of using a continuum of wavelengths thereby allowing for the development of a portable imaging device. The physiological markers may be measured using marker maps as described in further detail below. Alternatively, the raw spectra for these physiological markers may be processed using an artificial neural network, deep learning or a support vector machine to obtain measures that can be correlated with tissue viability.

For example, the images that are obtained with the portable imaging device are obtained while the tissue region is being illuminated by a light source that generates several separate monochromatic light signals having different, discrete wavelengths in the range of about 600 nm to about 1,000 nm. The images can then be combined and multispectral unmixing, which may also be referred to as multispectral decomposition, can then be used to obtain images or maps of certain physiological markers of interest such as, but not limited to, oxy-hemoglobin, deoxy-hemoglobin, total hemoglobin (tHb), oxygen saturation, methemoglobin (metHb), water, and melanin. Elevated levels of metHb are negatively correlated with tissue viability and wound healing. Accordingly, metHb can be used as a marker of negative tissue heath. In accordance with the teachings herein, small-scale optical elements are employed by the portable imaging device to detect MetHb. Previously MetHb was only imaged using more expensive, stationary equipment such as an MRI unit.

The measurements made by the portable imaging device can be calibrated using tissue mimicking phantoms that have known amounts of the physiological markers that are used in accordance with the teachings herein to indicate tissue health. The measurements can also be calibrated using MRI, which is a known gold standard for determining perfusion and oxygenation, methemoglobin and water content. With MRI, relaxivity can be measured and a hemoglobin measure can be derived from the known relaxivities. Furthermore, MRI can correlate features seen deep in tissues (e.g. micro and macro angiopathic disease of the peripheral vessels) to superficial changes that can be measured with the portable imaging device described herein.

Further calibration may be performed by using the portable imaging device in a study on patients with diabetes. The patients can be separated into three groups of increasing disease severity: 1) those without limb ischemia, 2) those with limb ischemia, and 3) those with a diabetic foot wound. For example, one or more of deoxyhemoglobin, oxyhemoglobin, methemoglobin, total hemoglobin, and oxygen saturation can be measured for these wounds using the portable imaging device and then correlated with the values obtained for these markers determined by MR imaging of these wounds. These correlations can be used to derive correction coefficients to apply to measurements made by the portable imaging device.

MRI is a very powerful imaging tool that can be used to image blockages in arteries and measure blood flow to tissue. Unfortunately, MRI is expensive, has limited medical access on demand, and is not practical for screening the limbs of patients with diabetes. Advantageously, the portable imaging device in accordance with the teachings herein is an inexpensive device that can be used with a remote server for screening patients for various physiological conditions in various settings.

Referring now to FIG. 1, shown therein is a block diagram of an example embodiment of a system that includes a portable imaging device that can be used for remote tissue assessment. The portable imaging device includes a light source unit 10 and a mobile device 12 having a camera 32. The mobile device 12 may be a smart phone or similar electronic device that has a camera. The light source unit 10 has a form factor that corresponds with the form factor of the mobile device 12 and an attachment mechanism that allows the light source unit 10 to releasably engage the mobile device 12. Accordingly, when a user wishes to use the portable imaging device to image a tissue region, the user can mount the light source unit 10 to the mobile device 12 and then obtain image data for several images of the tissue region while the light source unit 10 generates a light signal having a different discrete wavelengths to illuminate the tissue region for obtaining each image. Extra images are taken without illumination to obtain a reference image data set that is used for performing noise reduction on the other image datasets that are obtained of the tissue region under NIR and visible light illumination. The wavelengths of the light signal that illuminates the tissue region are generally in the visible light or NIR range and more specifically within the range of about 600 to about 1,000 nm. Accordingly, the camera 32 of the mobile device 12 is generally sensitive to the visible light or NIR range in order to be used with the light source unit 10.

The different discrete visible light and NIR wavelengths that are used during imaging are specifically chosen to measure a particular physiological marker of interest. The methodology that is employed only requires a small number of wavelengths which reduces the hardware requirements of the light source unit 10. In particular, N light signals are generated where N is the number of physiological markers being measured in the obtained images. The parameter N is an integer that is small such as, but not limited to, $N \leq 6$, for example. Accordingly, the light source unit 10 requires only N monochromatic light sources such as N monochromatic LEDs.

While the methodology employed herein reduces the hardware requirements for the light source unit 10 used by the portable imaging device, there is an increase in the computational complexity for measuring the N physiological markers using N image datasets that were obtained using N distinct discrete visible light and NIR wavelengths. This is because the N image datasets are combined and then multispectral unmixing can be used to measure a map for each physiological marker; hereafter referred to as a physiological marker map. Accordingly, N physiological marker maps are generated having the same size as the obtained image datasets where each physiological marker map is associated with a particular physiological marker. Furthermore, various image processing steps may be applied to the N image datasets to improve the quality of the N physiological marker maps that are produced. However, to improve processing speed, the N image datasets can be processed using a more power processor or a distributed set of processors that can be provided remotely such as by an analysis server 14, in this example embodiment.

The light source unit 10 includes a controller 20, a light source module 22 having a plurality of LED drivers with LEDs 22a to 22N, a communication unit 24 and a power module 26. The light source unit 10 may include additional or alternative elements in other embodiments. For example, instead of using LEDs that generate light having a single wavelength, LEDs may be used which are controllable to generate light at different discrete wavelengths. An example of the electronic components that may be used for the light source unit 10 is shown in FIGS. 5A-5D and FIG. 6.

In this example embodiment, the LEDs 22a to 22N are monochromatic, visible light or NIR, light emitting diodes that are controlled by the controller 20 which generates a light control signal that is sent to the light source module 22. The controller 20 can use the light control signal to control the LED drivers 1 to N to regulate both light intensity (e.g. <2% current ripple) as well as light duration (e.g. +/−8 microseconds) for the light signals that are generated by the LEDs 1 to N. The LEDs 22a to 22N are selected to have a particular wavelength in the range of about 600 nm to about 1,000 nm that is selected as being optimal (as described below) according to the physiological markers that are to be measured from the obtained image datasets.

The LEDs 22a to 22N are generally high powered (e.g. about 3-5 Watts) and larger amounts of power can be used for the LEDs that generate light at longer wavelengths to counteract the lower sensitivity of the camera 32 of the mobile device 12 at longer wavelengths. However, the intensity of the generated light signals depends on the sensitivity of the camera 32 to the visible light or NIR wavelengths used in these light signals. During manufacture, calibration may be run on different types of mobile devices that may be used with the light source unit. The calibration will scale the light intensity versus a known reflector and determine the intensity of light that will saturate the camera for each mobile device and further, generate values for parameters that control the light intensity for the generated light signals during use. These parameters can be stored in a look-up table in memory provided by the microcontroller and the parameters that correspond to the particular mobile device 12 being used with the light source unit 10 may be used in practice. During use, this calibration may be periodically repeated before image acquisition by introducing a reflector of known size and visible light or near IR absorbance in order to deal with cameras whose sensitivity changes over time. The reflector may be a spectralon or a didymium for example.

In an alternative embodiment, a larger number of visible light or NIR wavelengths and therefore a larger number of LEDs can be used to obtain more image data sets that can be used to reduce error in determining the values for the physiological marker maps. However, the footprint of the light source module 22 increases by the number of wavelengths required. For example, in the example implementation shown in FIGS. 5A-5D and 6, each additional wavelength adds about another 2 $cm^2$ to the physical footprint of the light source module 22.

The communication unit 24 is a Bluetooth radio. The controller 20 communicates over a Bluetooth Serial Port Protocol connection to the mobile device 12. The power module 26 provides power to the electronic components of the light source unit 10. Accordingly, the power module 26 generally includes a voltage regulator that can be coupled to a lithium polymer battery that is used to provide enough current to flow to the LEDs 22a to 22N. For example, the battery can be selected to provide about 2 A peak power to drive the LEDs 22a to 22N. The interface unit 28 includes off board connectors such as a battery connector (see FIG. 5B for example) to connect the power module 26 to the battery. In an alternative embodiment, the battery may be rechargeable in which case the power module 26 may also include a battery charger (see FIG. 5B for example).

In an alternative embodiment, the power module 26 is coupled to the mobile device 12 via an appropriate interface such as a USB interface to receive power from the mobile device 12. For example, the interface unit 28 can include a USB (i.e. Firewire interface) to allow the light source unit 10 to electrically connect to the mobile device 12 to receive power therefrom which is then regulated by the power module 26. The communication unit 24 allows the light source unit to communicate with a communication unit 34 of the mobile device 12 in order to synchronize the illumination of the tissue region with monochromatic visible or NIR light and image capture by the camera 32.

Figure 3B:
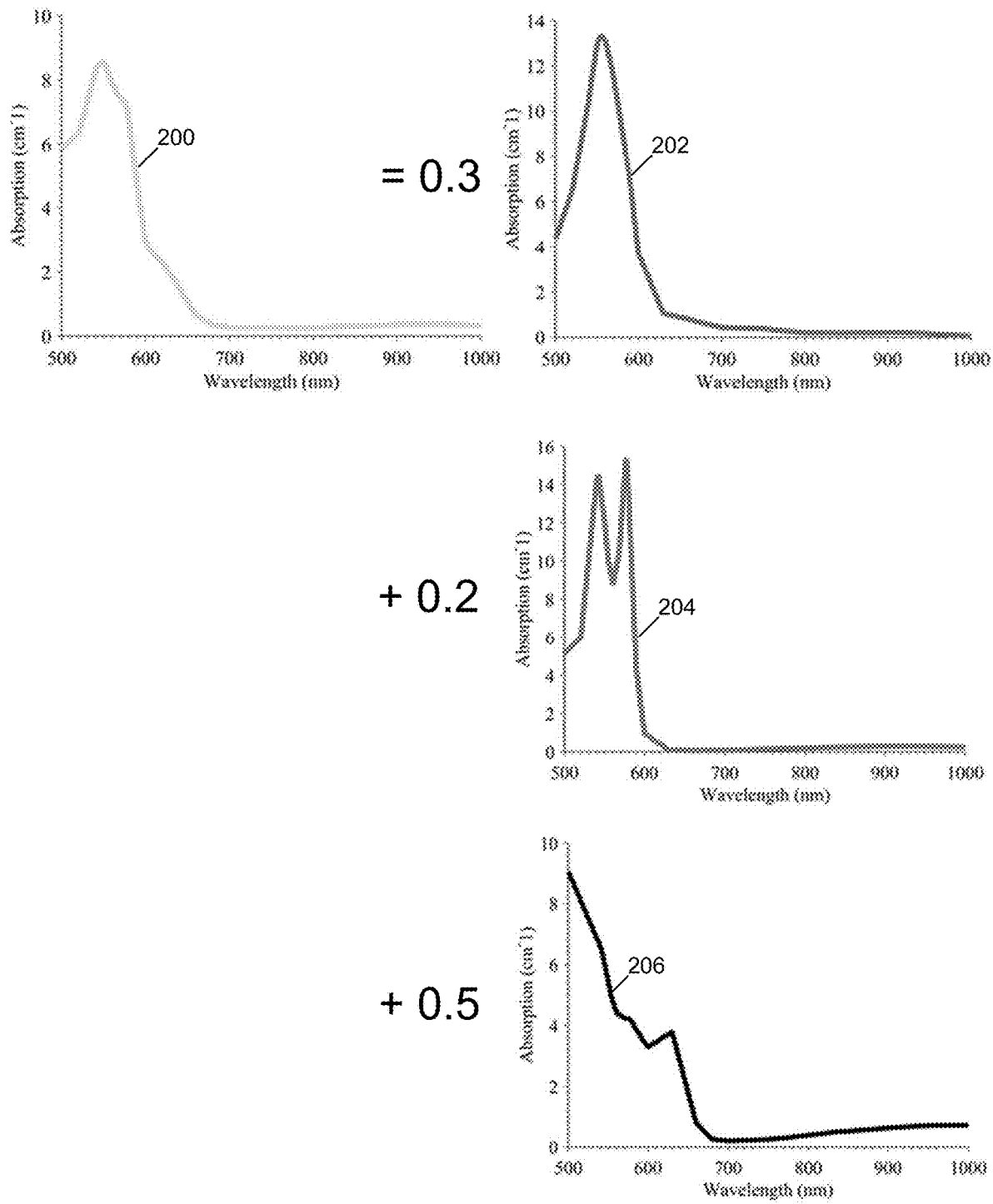
FIG. 3B is a graphical example of multispectral unmixing.

The N visible light or NIR wavelengths can be selected for their "optimal" distribution by minimizing the "condition number" of the error of the inversion matrix $A^{-1}$ where A is the matrix that is used during spectral unmixing as explained in further detail with respect to FIGS. 3A and 3B. The condition number represents the stability of this inversion. The visible light or NIR wavelengths that minimize the condition number of the inversion matrix are selected based on the absorption coefficients of the particular physiological markers that are used. Accordingly, the matrix A can be composed of the absorption coefficients for the N physiological markers of interest and an initial random set of N wavelengths between about 500 and 1,050 nm since the solution is non-monotonic. The absorption coefficients can be measured in the lab with respect to the physiological markers of interest or the absorption coefficients may be determined from known published standards for human tissue or animal tissue depending on the use of the portable imaging device.

A minimization routine such as, but not limited to, the Levenberg-Marquardt method, the Nelder Mead simplex method, the conjugate gradient method and Newton's method, for example may be used to solve for the minimum condition of the inversion matrix from a random starting seed of N wavelengths. The process of determining the minimum condition number from the starting seed can be iterated numerous times, such as $10^6$ times, to shift the wavelengths until the optimum wavelengths are obtained. The number of iterations depends on a minimum acceptable condition number. Looking at the absorption spectra, the selected optimal wavelengths are near points of inflection/minima of the first or second derivative (with respect to wavelength).

For example, the optimal wavelengths may be determined for the visible light or NIR light signals to separate the obtained image data into physiological marker maps for the physiological markers oxyhemoglobin, deoxyhemoglobin, methemoglobin, melanin, collagen and water. These wavelengths can be about 620, 630, 700, 810, 880 and 940 nm, respectively.

The water imaging map may be used for diagnosis of hydration and edema at the tissue region. Water monitoring is important for end points of resuscitation, burn edema, sepsis and infection and any medical condition for which the movement of water from the intravascular space to the interstitial space is of consequence. For example, in burn wounds water moves from the intravascular space to the interstitial space secondary to leaky vessels. This contributes to the over-resuscitation that occurs in the early period post injury and conditions that cause fluid creep, compartment syndromes and mortality.

Water marker maps may also be useful for determining relative hydration in the skin. This marker map could indicate regions of tissue that are prone to becoming rough and flaky. Small tears can lead to fissures which can lead to larger more long term, wounds with serious complications. Water marker maps may be useful in identifying regions of tissue requiring more hydration through creams or other topical treatments.

Melanin marker maps could be useful in aiding with determination of hyperpigmentation following scarring of wounds. A whitening procedure is often performed to reduce melanin concentration in the epidermal layer and such melanin maps could be used to monitor progression and regression of melanin deposition in skin, scar, and surrounding tissue.

The collagen marker map may be used to monitor the health of the dermal matrix of the tissue region. The type of collagen in the wound is a marker of maturity. It can be used to monitor wound healing, scar outcome and progression. For example, collagen morphology and orientation is associated with different types of scarring. For instance, a more parallel orientation is associated with hypertrophic scarring. The ability of the portable imaging device to delineate between these morphologies permits better treatments for scars.

The mobile device 12 includes a processing unit 30, the camera 32, the communication unit 34, a power unit 36, a user interface 38, and a storage unit 40. The storage unit 40 can be used to store various software code such as code for an operating system 42, computer programs 44, and a data store 46. The mobile device 12 also includes an imaging acquisition module 48 that can be used to control the light source unit 10 and the camera 32 for obtaining the N image datasets. The embodiment of the mobile device 12 shown in FIG. 1 is an example and there can be additional or alternative elements that are included in other embodiments of the mobile device 12.

The processing unit 30 controls the operation of the mobile device 12 and includes one or more suitable processors that can provide sufficient processing power depending on the configuration and requirements of the mobile device 12 as is known by those skilled in the art. For example, the processing unit 50 may be one or more high performance processors. In alternative embodiments, specialized hardware can be used to provide some of the functions provided by the processing unit 30. The processing unit 30 communicates with at least one device, such as the communication unit 34 and/or the user interface 38, in order to receive or send data. The other components of the mobile device 12 that are similar to the components of the analysis server 14 may operate in a similar manner.

The mobile device 12 is running or executing the imaging acquisition module 48 which may be implemented as a software application that coordinates the communication between the mobile device 12 and the light source unit. The imaging acquisition module 48 also controls the camera 32 to capture at least N+1 image datasets, with N images datasets being acquired during illumination of the tissue region using different unique visible light or NIR wavelengths and one image dataset is captured without any illumination of the tissue region by the light source unit 10.

Accordingly, the camera 32 is used to capture the image datasets of interest. The camera 32 can be activated for about 1 second to obtain an image to minimize any noise in the obtained image dataset that is due to patient motion. The camera 32 can be a conventional CCD image capture device that is naturally sensitive to visible or NIR light in the range of about 1,000 nm, which is sufficient for the purposes of spectral unmixing in the NIR region. Calibration can be performed for the sensitivity of the camera 32 to visible or NIR light by using a small marker or reflector that is included in each image as explained previously. Using a marker of known reflectance, both the sensitivity of the camera 32 as a function of wavelength as well as the relative amount of absorption from these wavelengths can be accurately determined. Calibration can also be performed for visible color and size as is known by those skilled in the art.

The N+1 image datasets are stored on the data store 46 and can then be sent to the analysis server 14 by the communication unit 34. The communication unit 34 uses a communication protocol that corresponds to the communications protocol being used by the communications network 16 that links the mobile device 12 and the analysis server 14. Advantageously, the computing power of the analysis server 14 can be used to process and analyze the image datasets obtained by the portable imaging device. This allows for the wide dissemination of the portable imaging device as it does not have a high amount of processing power which leads to cheaper and simple implementation unlike stand-alone imaging devices, like an MRI unit, or devices that necessarily have to integrate into a "hospital" infrastructure.

The analysis server 14 generally includes a number of functional components for facilitating the provision of a web portal that is accessed by users of the portable imaging device so that the users can send the obtained image datasets to the analysis server 14 for image processing and analysis. The analysis server 14 includes a processing unit 50, a communication unit 52, a user interface 54, and a storage unit 56. The storage unit 56 is similar to the storage unit 40 and includes software code for an operating system 58, computer programs 60 and a data store 62. The analysis server 14 further includes a web portal module 64, an image processing module 66 and an image analysis module 68. The analysis server 14 further includes several power supplies (not all shown) connected to various components of the server 14 for providing power thereto as is commonly known to those skilled in the art. The analysis server 14 is provided as an example and there can be other embodiments of the analysis server 14 with different components or a different configuration of the components described herein.

The analysis server 14 may be implemented in a variety of ways such as a desktop computer, a distributed computing network or cloud components. In some embodiments, there may be multiple analysis servers that work together to provide image processing and analysis especially in cases where there are many users who access the analysis server 14. For example, there may be multiple backup network servers (not shown) that may duplicate some or all of the functionality provided by the analysis server 14 and the data stored on the data store 62. The backup servers may also be used to prevent undesired data loss and for data recovery in certain events.

The processing unit 50 controls the operation of the analysis server 14 and can be one or more suitable processors that can provide sufficient processing power depending on the configuration and requirements of the analysis server 14 as is known by those skilled in the art. For example, the processing unit 50 may be one or more high performance processors. In alternative embodiments, the processing unit 50 may include several processors with each processor being configured to perform different dedicated tasks. The processing unit 50 communicates with at least one device, such as the communication unit 52 and/or the user interface 54, in order to receive or send data.

The communication unit 52 can be any radio and/or interface that allows the analysis server 14 to communicate with other devices or computers through the communications network 16 or another network. In some cases, the communication unit 52 can include at least one of a serial port, a parallel port or a USB port that provides USB connectivity. Additionally, or alternatively, the communication unit 52 can also include at least one of an Internet, a Local Area Network (LAN), an Ethernet, a Firewire, a modem or a digital subscriber line connection. Additionally, or alternatively, the communication unit 16 may be a radio that communicates utilizing CDMA, GSM, GPRS or Bluetooth protocol according to standards such as IEEE 802.11a, 802.11b, 802.11g, or 802.11n.

The user interface 54 can be any suitable input/output device that allows an administrator to operate and interact with the analysis server 14. The user interface 54 may include a display that provides visual information depending on the configuration of the analysis server 14. For instance, the display can be a cathode ray tube, a flat-screen monitor, an LCD-based display and the like depending on the implementation of the analysis server 14. The user interface 54 can further include at least one of a mouse, a keyboard, a touch screen, a thumbwheel, a track-pad, a track-ball, a card-reader, voice recognition software and the like again depending on the particular implementation of the analysis server 14. The user interface 54 may also include I/O hardware such as, but not limited to, at least one of a microphone, a speaker and a printer, for example.

The storage unit 56 can include RAM, ROM, one or more hard drives, one or more flash drives or some other suitable data storage elements such as disk drives, etc. The storage unit 56 may be used to store an operating system 58, computer programs 60 and a data store 62, as is commonly known by those skilled in the art. For instance, the operating system 58 provides various basic operational processes for the analysis server 14. The computer programs 60 include various user programs so that a user can interact with the analysis server 14 to perform various functions such as, but not limited to, at least one of acquiring data, data analysis, providing treatment recommendations as well as sending and receiving messages.

The data store 62 can be configured to provide a centralized secure database to store image data obtained from the various portable imaging devices. The image data can be associated with various user profiles for users from which the image data was obtained. The image data can be obtained for a given user can be obtained at different time periods so that comparison across time can be made for a user to determine the onset of a physiological condition at the tissue region and/or the progression of the physiological condition. Accordingly, the data store 62 includes one or more databases that are used to store the image data and user profile data. The database can also store other information required for the operation of the computer programs 60, and the operating system 58 such as dynamically linked libraries and the like. The databases can be accessed by applications that are executed by the analysis server 14. The databases may be implemented as a relational database such as an SQL database. Additionally or alternatively, a separate computing device may host at least some portions of the storage unit 56.

The mobile device 12 and the analysis server 14 communicate via the communications network 16. The communications network 16 can be any suitable communication network depending on the particular implementation of the overall system. For example, the portable imaging device may be used in a medical institution in which case the communications network 16 may be an internal institutional network, such as a hospital network, that may be implemented using suitable type of network architecture and communication protocol such as an Intranet. In other cases, the communications network 16 can be an external network such as the Internet or another external data communications network, which is accessible by using a web browser on the mobile device 12 to browse one or more web pages presented over the Internet by the web portal module 64.

The web portal module 64 is used to provide and host a website or a network portal (which can include an FTP site, or an SSH or another form of electronic interface other than a website) that can be accessed by the users of the portable imaging device so that these users can use the analysis server 14 to analyze the images that they obtain using the portable imaging device. In particular, the web portal module 64 is configured to allow users to setup an account and upload the obtained image datasets. The web portal module 64 also allows users to enter other information related to the obtained image datasets such as the date on which the image datasets were obtained. In some embodiments, the web portal module 64 can also allow the user to enter the location of the tissue region that was imaged. In some embodiments, the web portal module 64 can allow the user to enter the physiological conditions that are being assessed at the tissue region.

The web portal module 64 also provides web pages that show the analysis results of the image datasets that have been uploaded at a particular date. In some embodiments, the web portal module 64 can also show various metrics related to the tissue region that can be derived from the physiological markers that are used to analyze the image datasets. In some embodiments, the web portal module 64 can also display the values of the metrics for different time periods for which image datasets were obtained to allow the status of the physiological condition to be tracked over time. In some embodiments, the web portal module 64 can also provide a diagnosis or a recommendation to the user such as a message to go see their health care provider when the tissue region exhibits a physiological condition with a certain status, such increasing tissue non-viability or a negative progression of a diabetic foot ulcer, for example.

The image processing module 66 is used to pre-process a collection of image datasets that have been obtained for a user at a particular date. The pre-processing is done to remove noise and improve the Signal to Noise Ratio (SNR) for the various physiological markers of interest that will be measured from the obtained image datasets. The operation of the image processing module 66 is described in further detail with respect to FIGS. 2 and 3A.

The image analysis module 68 is used to analyze a pre-processed collection of image datasets in order to determine one or more physiological marker maps. Various measurements may be performed on the determined physiological marker maps to determine whether a particular physiological condition exists at the tissue region from which the collection of image datasets was obtained. If the image analysis module 68 determines that a particular physiological condition exists, then the image analysis module 68 may perform further actions to determine the severity of the physiological condition and to generate a warning signal that is displayed to the user via the web portal or otherwise sent to the mobile device 12 that is used by the user to notify the user to take a particular action such as seeing their medical caregiver (e.g. EMS, nurse, clinician, doctor, and the like) for further assessment and possibly treatment of the tissue region. Alternatively, the image analysis module 68 may be used to automatically monitor and alert a care team to sudden changes in tissue properties. The operation of the image analysis module 68 is described in further detail with respect to FIGS. 2, 3A and 3B.

The processed image datasets, the physiological marker maps and/or the measurements may be sent back to the mobile device 12 via the communication network 16. Additionally, or alternatively, the processed images, the physiological marker maps and/or the measurements may be available through the web portal that can be accessed by the user. Additionally, or alternatively, the processed images, the physiological marker maps and/or the measurements may be directly sent to another repository such as, but not limited to, an electronic medical record or an e-consult interface, for example.

In alternative embodiments, the web portal module 64, the image processing module 66 and the image analysis module 68 may be combined or may be separated into further modules. The web portal module 64, the image processing module 66 and the image analysis module 68 are typically implemented using software. For ease of understanding, certain aspects of the methods described in accordance with the teachings herein have been described as being performed by one of the web portal module 64, the image processing module 66 and the image analysis module 68 but it should be noted that these methods are not limited in that respect, and the various aspects of the methods described in accordance with the teachings herein may be performed by other modules.

Referring now to FIG. 2, shown therein is a flowchart of an example embodiment of a remote tissue assessment method 100. At act 102, the method 100 involves selecting imaging parameters for obtaining a collection of image datasets of a tissue region of interest. The parameters can be chosen depending on the tissue region that is being imaged and the physiological condition that is being tested or monitored. For example, the portable imaging device may be calibrated for measuring six physiological markers in total but during use a user may input the tissue region being imaged and the physiological condition being tested/monitored and the best combination of physiological markers from the six physiological markers that have been calibrated are then chosen for obtaining the image datasets and the corresponding measurements. Accordingly, while the description has previously described using N LEDs and obtaining N+1 image datasets for measuring N physiological markers, there may be instance in which M physiological markers are used and M+1 image datasets are obtained wherein M is an integer and M≤N. In other words, there may be cases in which not all six physiological markers are needed. For example only two physiological markers may have to be used in which case M=2 and the 2 LEDs having the wavelengths that have been determined to be optimal for the two physiological markers that have been selected for imaging are identified. The parameters for the light control signal for these identified LEDs are also initialized based on previous calibration (e.g. for light intensity) when using these two LEDs for imaging with a particular camera provided by the mobile device.

The method 100 then proceeds to act 104 at which point the image datasets for M+1 images are obtained. Image data sets for M images are sequentially obtained while sequentially activating each of the identified M LEDs to use a visible light or NIR wavelength to illuminate the tissue region, and a reference image dataset is obtained of the tissue region without illuminating the tissue region.

The method 100 then proceeds to act 106 at which point the obtained image datasets are processed to remove noise in order to improve SNR and the accuracy of the image analysis and measurements that are later performed. Various image processing methods can be used to denoise the image datasets as deemed appropriate.

For example, referring now to FIG. 3A, shown therein is a flowchart of an example embodiment of an image processing method 150 that can be used with the remote tissue assessment method 100.

Act 152 of the image processing method 150 involves performing light distribution correction for each of the image datasets that have been obtained including the reference image dataset. The light distribution correction may be implemented by applying top hat filtering to each of the image datasets to correct for uneven light distribution across the image datasets. In alternative embodiments, the light distribution correction can be implemented by adjusting the light intensity in the image using a low order, 2 dimensional polynomial or a 2D Gaussian fit to the light distribution.

Act 154 of the image processing method 150 involves applying non-intensity based image registration to each of the image datasets that have been obtained including the reference image dataset. This may be done by rigidly registering the image datasets using mutual information or another non-intensity based similarity metric. This can involve randomly rotating and shifting a 'moving' image with respect to the reference image. A similarity metric is then determined (either MI, or an edge metric (e.g. Prewitt, Laplace, Sobel) that is not dependent on image intensity). The registration will then try to find an optimum rotation and shift that minimizes this similarity metric. This is done so that the tissue region in the various image datasets can be aligned allowing some of the image datasets to be added together or subtracted from one another in one or more of the following steps of the image processing method 150, while not distorting the tissue region in the image datasets.

Act 156 of the image processing method 150 involves performing image subtraction by subtracting the registered reference image dataset (that was obtained without illuminating the tissue region) from the other registered image datasets to produce M reflectance datasets for the M physiological markers that are each associated with a different wavelength that was used for illuminating the tissue region during image capture.

Act 158 of the image processing method 150 involves performing image denoising on the M reflectance datasets by using local averaging on each reflectance dataset. For example, 3×3 median filtering may be applied to each 3 by 3 overlapping subset of data points in each reflectance dataset to eliminate noise spikes in the reflectance dataset. In alternative embodiments, the 2D Adaptive Wiener filtering, or moving average filtering can be used.

Act 160 of the image processing method 150 involves performing hyper-spectral unmixing to obtain the M physiological marker maps. This may be done in a variety of ways including using constrained, multivariate minimization multispectral unmixing on a pixel by pixel basis based on previously measured absorption coefficients for each physiological marker at each of the M illumination wavelengths.

The result is that marker maps for the physiological markers of interest are obtained. For example, the marker maps may be one or more of an oxyhemoglobin marker map, a deoxyhemoglobin marker map, a methemoglobin marker map, a melanin marker map, a water marker map and a collagen marker map.

The input to the hyper-spectral unmixing act 160 is the M reflectance datasets and the pixel by pixel intensity of the marker maps is the solution to equation 1 for each of the M wavelengths.

$$I(x,y) = i(1)*A(1) + \ldots + i(M)*A(M) + b \quad (1)$$

In equation 1, x and y are pixel coordinates in the reflectance dataset matrix I, $I(x,y)$ is the measured reflectance intensity at pixel $(x,y)$ for a given illumination wavelength used to illuminate the tissue region during image capture, $i(k)$ is the relative contribution at pixel x,y of a particular physiological marker k to $I(x,y)$, the absorption coefficient $A(k)$ is the absorption of the $k^{th}$ physiological marker at the given wavelength, k is an integer from 1 to M where $\Sigma_{k=1}^{m} i(k) = 1$ and all $i(k) \geq 1$.

The parameter b is an offset term. The absorption coefficients $A(k)$ can be determined a priori as explained previously. Equation 1 can be replicated M times using the M reflectance datasets for each of the M illumination wavelengths that were used to obtain the M image datasets. This then sets up a matrix equation with M equations and M unknowns (i.e. the $i(k)$ coefficients). The unmixing method then determines the constrained, least squares solution to obtain the values for $i(k)$, k=1 to M at each pixel x, & y.

Referring now to FIG. 3B, shown therein is a graphical example of multispectral unmixing. The spectra 200 is a resultant spectra that involves the spectra of three different species (e.g. markers), e.g. the spectra 202 of 30% deoxyhemoglobin, the spectra 204 of 20% oxyhemoglobin and the spectra 206 of 50% methemoglobin. The task of unmixing involves determining, based on knowing the component spectra 202, 204 and 206, which species are most likely to give the resultant spectra 200.

An alternative to using hyper-spectral unmixing at act 160 is to use a learning or neural network methodology to generate a positive/negative test result. This may be done by collecting a large number of image data sets with measured known outcomes through time. This data will contain the spectral information for physiological changes over time which will correlate with a positive or negative outcome. By training a feed-forward neural network on this data, algorithms can be developed that can predict outcome based on similarity to previously measured spectra.

Act 162 of the image processing method 150 involves performing output denoising on the M marker maps that are generated by the multispectral unmixing. Denoising may be performed by using adaptive filtering (e.g. a Wiener low pass locally adaptive filter). In alternative embodiments, denoising may be performed by applying median filtering or moving average filtering.

It should be noted that in an alternative embodiment of the image processing method 150, only the multispectral unmixing act 160 is performed. All of the other steps are optional in that while they improve image quality and SNR, there may be some cases in which they are not needed. However, in the absence of other image processing acts to improve SNR, the unmixing method will be corrupted by noise, such as electronic noise from the camera of the mobile device, electronic noise due to stray light sources, and physiological noise (e.g. movement).

Referring again to FIG. 2, the remote tissue assessment method 100 then proceeds to act 108 at which point the M marker maps are analyzed to determine the existence of a particular physiological condition at the tissue region or to monitor the status of a certain physiological condition at the tissue region. Measurements may be performed on a signal physiological marker map or measurements may be made after combining two or more physiological marker maps to generate another marker map. For example, the analysis may involve determining a value for total hemoglobin which results from combining an oxyhemoglobin marker map, a deoxyhemoglobin marker map and a methemoglobin marker map to generate a total hemoglobin marker map from which various measurements can be made. Another measurement that can be made is oxygen saturation which can be determined from dividing the oxyhemoglobin marker map by the total hemoglobin marker map. Another measurement may be made on the methemoglobin marker map by itself, such as determining a methemoglobin distribution or measurement value. Alternatively, another measurement that may be made is on a water marker map. In another alternative, another measurement that may be made is on a collagen marker map. For any of these marker maps or a combination of these marker maps, threshold values (e.g. minimum total hemoglobin, minimum oxygenation, maximum methemoglobin) can be used to identify areas that are outside normal ranges. If there are portions of the tissue regions for which measurements are outside of normal ranges, an alert can be generated to a care team to notify them that there is tissue at risk.

Once the measurements are made, the measurements can be compared to a threshold value to determine if there is a particular physiological condition that requires further analysis. Alternatively, the measurements may be monitored for changes over time. For example, a user may obtain a collection of image dataset at certain time periods such as every 6 hours or every day. Measurements obtained at a subsequent time period can be compared to measurements obtained at a preceding time period to determine if there is a sudden change in the measurement which may require further assessment.

The method 100 then proceeds to act 110 at which point a recommendation and/or status update is provided depending on the circumstances in which the portable imaging device is used. For example, any sudden changes in measurements (e.g. decreases or increases depending on the physiological marker) for certain time periods may trigger a reminder or warning message that can be sent to the portable imaging device so that the user receives it and/or may be a message that is generated and send to the medical caregiver to to perform further tissue assessment or to perform a treatment on the tissue region.

It should be noted that there various challenges have been overcome in using a portable handheld imaging device to obtain image datasets of a tissue region and then processing the obtained image datasets to obtain the various measurements that are used to assess a tissue region for a particular physiological condition or monitor the status of a physiological condition at the tissue region.

For example, the melanin content of the skin or skin pigmentation as well as the keratin layer of an ulcer can have an effect on the light that is reflected during image acquisition. The melanin can be particularly challenging especially when imaging is done from the bottom of the foot to the top as in a black person which may change the measurement result. However, with the portable imaging device described in accordance with the teachings herein illumination wavelengths and LEDs can be chosen to penetrate the skin surface of the tissue region for the top of a user's foot.

Furthermore, in some cases, the "shiny" part of the wound will cause specular reflectance or act as a mirror which can have an effect on image capture. However, a series of image datasets can be obtained under varying amounts of exposure to intentionally underexpose the obtained images. The reconstruction will then extend the captured dynamic range of the camera of the mobile device that will account for this specular reflection.

The curvature of the tissue region being imaged such as the curvature of the foot or the surface area, can also have an effect on image capture for conventional devices. However, curvature is not an issue for the portable imaging device described in accordance with the teachings herein, curvature since the path length does not have to be maintained in a standardized way since it is the change in the measurement values on the tissue region can be used to determine the status of a physiological condition at the tissue region rather than absolute values.

Furthermore, conventional imaging devices may have to be held a certain distance away from the tissue region that is being imaged since the conventional devices are calculating concentrations or ratios of certain values. This is not needed with the portable imaging device provided by the teachings herein which provides more flexibility and ease of use of the portable imaging device when obtaining images for the same reasons given previously for dealing with a tissue region that has a curvature.

Referring now to FIGS. 4A-4D, shown therein are various views of an example embodiment of a housing 250 that can be used for the light source unit 10. The housing 250 has an attachment mechanism that can releasably engage the housing of the mobile device 12 in a "snap-on" and "snap-off" fashion. This allows the light source unit 10 to be easily attached or detached to a variety of mobile devices and can interact with the various cameras that are used in the mobile devices without any impact to the image quality of the obtained image datasets and subsequently clinical assessment that is based on the obtained image datasets.

The housing 250 includes a base member 252 that is generally planar with an aperture 262, upper and lower walls 254 and 256 and two opposing side walls 258 and 260. The walls 254 to 260 are disposed inwardly with respect to the planar surface of the base member 252. The opposing side walls 258 and 260 are spaced apart to releasably receive edges of the mobile device so that the housing 250 can be attached to the mobile device in a "snap-on" fashion and removed in a "snap-off" fashion. Accordingly, the height of the upper wall 254 is less than the side walls 258 and 260 to allow the mobile device to be slide into the housing 250 from the top portion of the housing 250.

The base member 252 further includes inner walls 264, 266 and 268 and an aperture 262 that is bounded by a portion of the upper wall 254, the inner wall 264 and a portion of the side wall 260. The aperture 262 is disposed at a location that corresponds with a location of the camera of the mobile device when the housing 250 is mounted to the mobile device. The light source module that has the LEDs is mounted within the housing 250 at the aperture 262 so that the light generated by the LEDs is not blocked by any portion of the housing 250. The light source module also has an aperture so that the aperture of the camera of the mobile device is not blocked (see FIG. 6 for an example implementation of the light source module).

The inner walls 266 and 268 and a portion of the side wall 260 form a compartment 267 which can be used to house certain electronic components of the light source unit such as a battery, for example. Inner wall 270 is located near the bottom wall 256 of the housing 250 and together with the inner wall 268, and the side wall 258 provide another compartment which may be used to house certain electrical components of the light source unit or may be used to provide an air gap between the mobile device and the light source unit to allow for the dissipation of heat during use.

The housing 250 also includes a slot 272 in the lower wall 256, a slot 263 in an upper portion of the side wall 260 and a slot 259 in an upper portion of the side wall 258. The slots 259, 263 and 272 may be used to access control input mechanisms like a button or toggle slider on the mobile device 12.

Figures 5A, 5B:
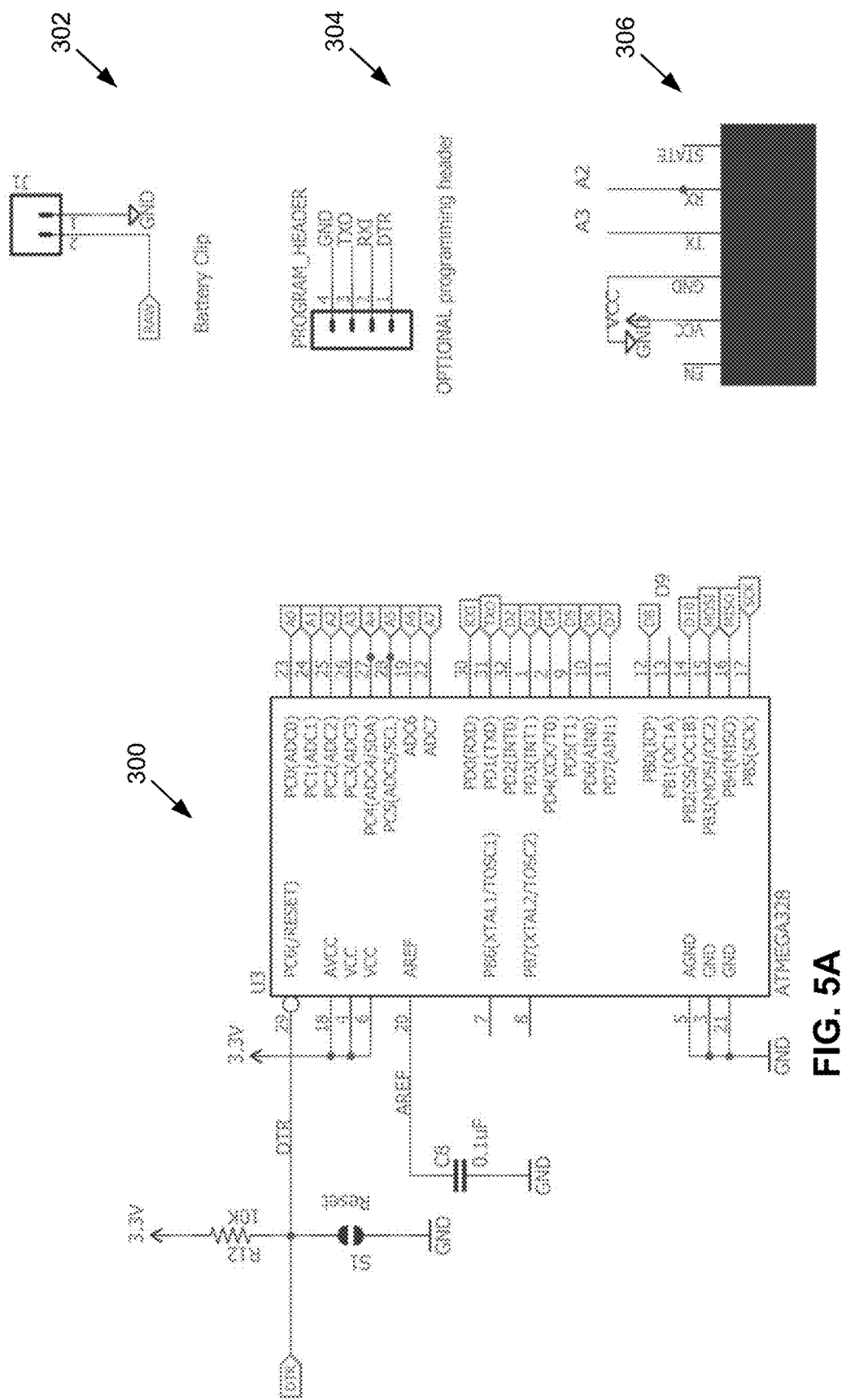
FIGS. 5A, 5B, 5C, and 5D show schematics of an example embodiment of electronic components which may be used with the light source unit of FIG. 1.
Figure 5C:
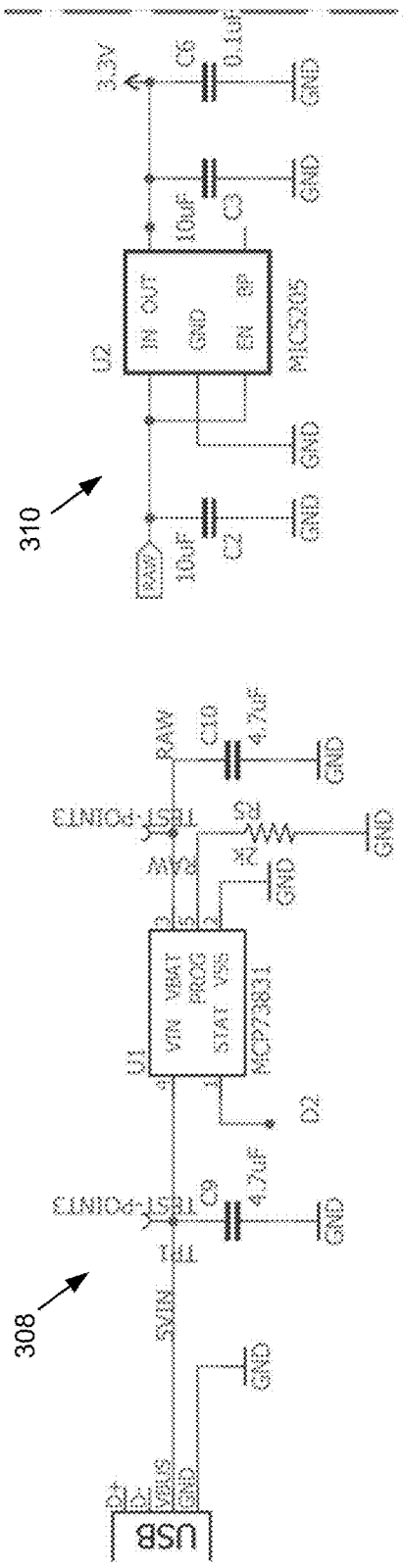
Figure 5D:
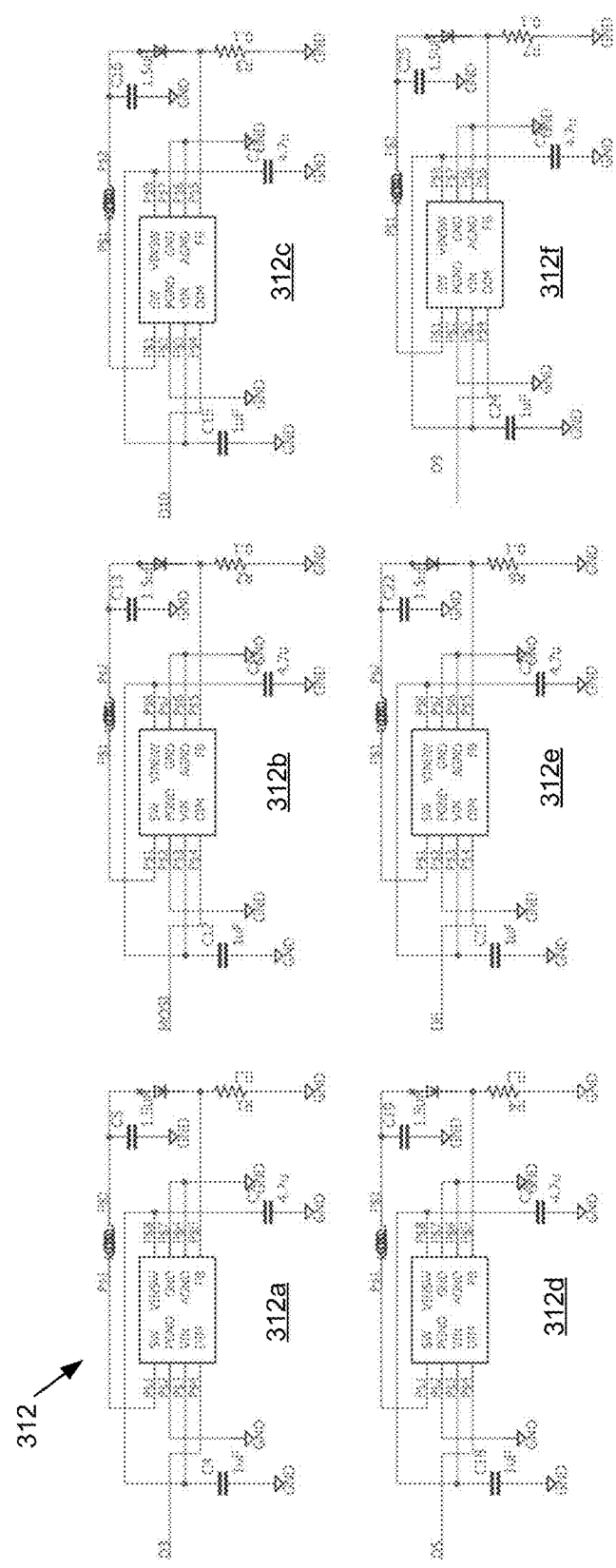

Referring now to FIGS. 5A-5D, shown therein are schematics of an example embodiment of electronic components which may be used with the light source unit 10. FIG. 5A shows the controller circuitry 300. FIG. 5B shows the off board connectors that can be used with the interface unit. The off-board connections include a battery clip 302 for connecting to a battery, an optional program header 304 for programming the controller and a Bluetooth connection 306. FIG. 5C shows battery charger circuitry 308 and power regulation circuitry 310 that can be used by the power module 26. FIG. 5D shows the power LED regulators 312a to 312f (i.e. LED drivers) for the various LEDs of the light source module 22. The Bluetooth connection 306 is a "universal" interface between the mobile device and the light source unit. In alternative embodiments, the Bluetooth connection 306 can be replaced and the battery charger circuitry 308 can be replaced with one or more wires that provide power & data communication.

Figure 6:
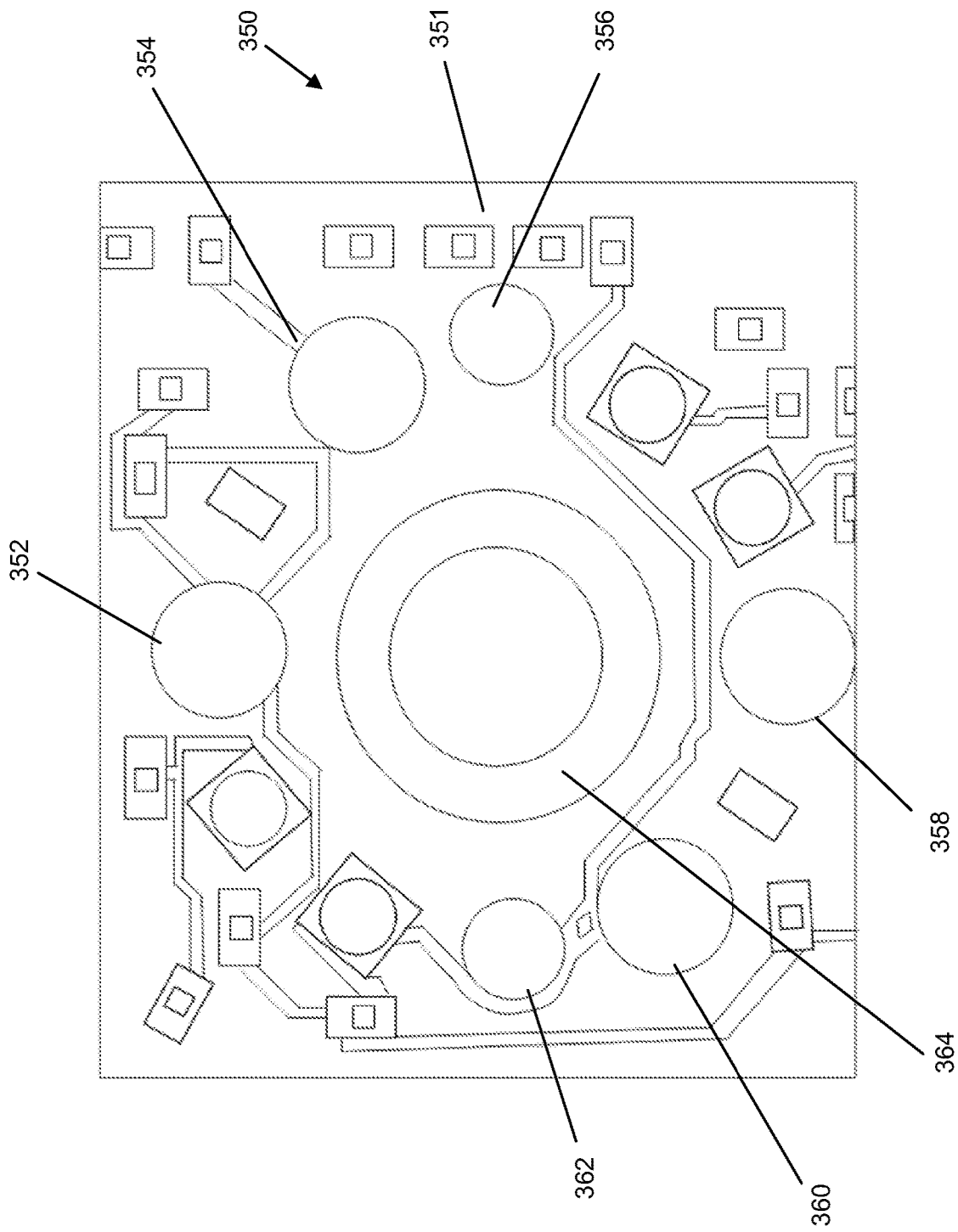
FIG. 6 shows an image of an example embodiment of a light source module that can be used with the light source unit of FIG. 1.

Referring now to FIG. 6, shown therein is an image of an example embodiment of a light source module 350 that can be used with the light source unit 10. The light source module 350 includes a printed circuit board 351 with various electrical components including LEDs 352 to 362. The light source module 350 also includes an aperture 364 in the printed circuit board 351. The LEDs 352 to 362 are disposed around the aperture 364. The aperture 364 is located to align with the aperture of the camera of the mobile device 12 so that the camera can acquire image data without any part of the light source module 350 being in the way so that the light source module 350 is not part of any of the acquired images. The light source module 250 is disposed at the compartment 262 of the housing 250 such that the LEDs are oriented towards the planar member 252.

While the teachings herein have been described in the context of assessing tissue regions of diabetic limbs, these teachings can also be applied to assessing the tissue regions for other types of physiological conditions. Examples of these other physiological conditions include, but is not limited to, post mastectomy and breast reconstruction, burns, sepsis, end points of resuscitation, limb monitoring in Intensive care units, acute and chronic wound monitoring, skin cancers, peripheral vascular disease, and triage in the field (e.g. military operations where decisions may need to be made between amputation versus non-amputation in the field).

In an alternative embodiment, in which the mobile device 12 has a sufficient amount of computational power, the image processing and image analysis of the image datasets that was described as being done on the analysis server 14 can alternatively be done on the mobile device 12. In such embodiments, the equations that are used for hyper-special unmixing can be simplified or an alternative processing methodology can be used such as an artificial intelligence/ machine learning platform that will not involve any multi-spectral unmixing. The neural network platform requires "ground truth" data on which to train, which can be obtained from performing studies on patients.

Figure 7A:
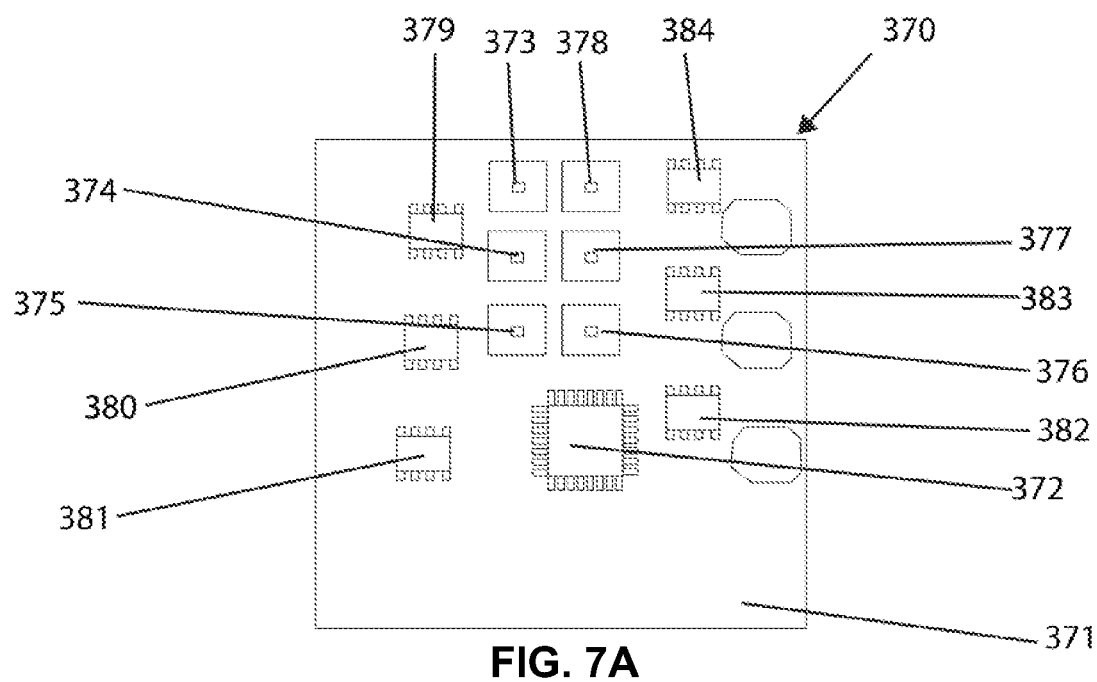
FIG. 7A shows a top image of an example embodiment of a printed circuit board having a light source module disposed thereon.
Figure 7B:
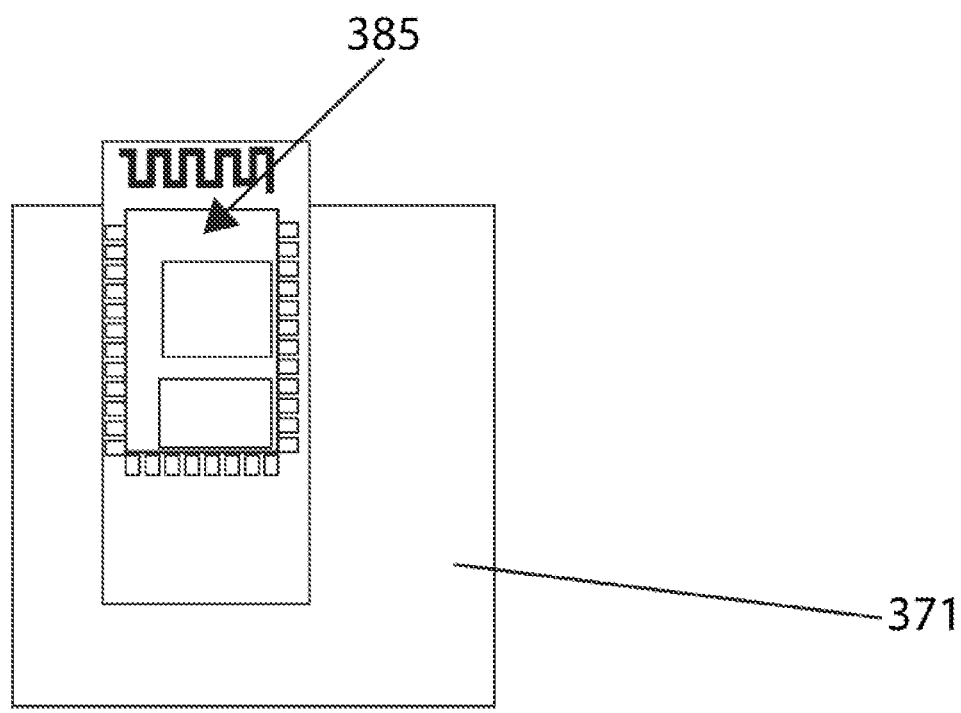
FIG. 7B shows a bottom image of the example embodiment of the printed circuit board having the light source module disposed thereon.

Referring now to FIG. 7A, a top image of an example embodiment of a printed circuit board 371 having a light source module 370 disposed thereon is shown. FIG. 7B shows a bottom image of the example embodiment of the printed circuit board 371 having the light source module 370 disposed thereon.

As shown in FIG. 7A, LEDs 373 to 378 and LED drivers 379 to 384 of the light source module 370 are disposed on the top surface of printed circuit board 371. A microcontroller 372 is also disposed on the top surface of the printed circuit board 371. This example embodiment may include an aperture, such as the one described above with respect to FIG. 6. However, an aperture is not shown in FIG. 7A so that the electronic components disposed on the printed circuit board 371 may be easily seen.

Still referring to FIG. 7A, according to one or more embodiments, microcontroller 372 drives LEDs 373 to 378 via LED drivers 379 to 384, where each LED 373 to 378 is connected to a corresponding LED driver 379 to 384 of the light source module 370. In some embodiments, microcontroller 372 may control LED drivers 379 to 384 to drive LEDs 373 to 378 in the same way that controller 20 controls LED drivers 1 to N to drive LEDs 22a to 22N, as previously described in this disclosure.

Referring now to FIG. 7B, a bottom image of the example embodiment of the printed circuit board 371 having the light source module 370 disposed thereon is shown. As shown in FIG. 7B, according to one or more embodiments, a Bluetooth module 385 may be disposed on a bottom surface of the printed circuit board 371. For example, the microcontroller 372 shown in FIG. 7A may communicate over a Bluetooth Serial Port Protocol connection (or other possible connection) to a communication unit of an associated mobile device using the Bluetooth module 385. In this way, according to one or more embodiments, the Bluetooth module 385 may communicate in the same way as the communication unit 24, as previously described in this disclosure.

Figure 8:
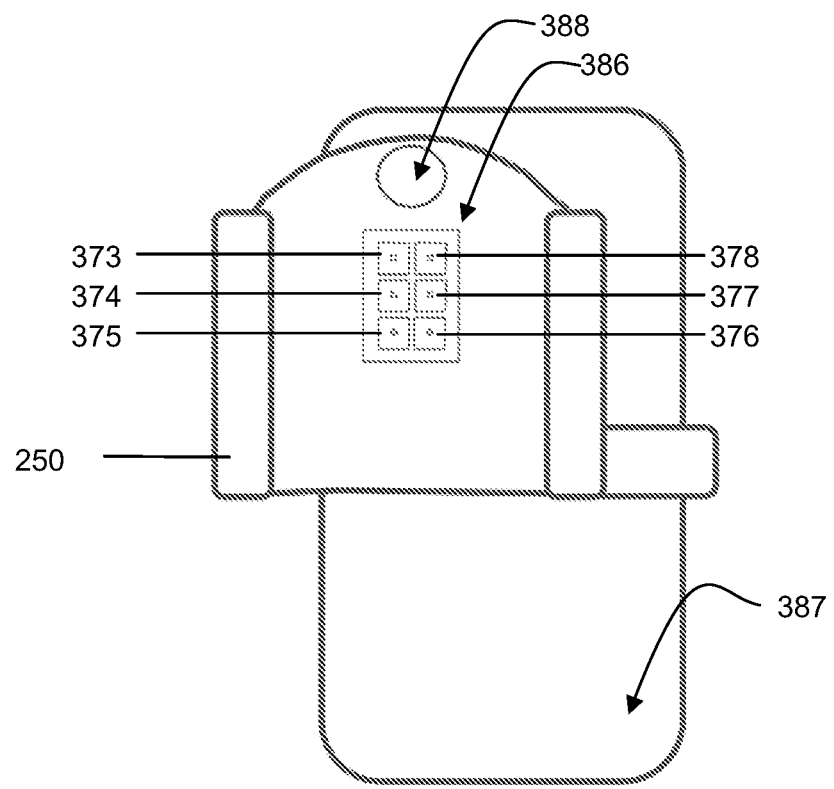
FIG. 8 is an image of an example embodiment of a housing of a light source unit.

Referring now to FIG. 8, an image of an example embodiment of a housing 250 of a light source unit is shown. As shown in FIG. 8, the housing 250 is a clip-on case according to some embodiments. In this way, the housing 250 shown in FIG. 8 is able to house the light source module of one or more embodiments and clip onto an associated mobile device 387 having a camera. According to one or more embodiments, the housing 250 includes an aperture 386, which allows LEDs 373 to 378 of the light source module 370 to pass unmodified by the housing 250. In some embodiments, a diffusive element may be placed on one or more of LEDs 373 to 378 to both obscure the one or more LEDs and create a more even light distribution profile. According to one or more embodiments, the aperture 386 is disposed at a location that corresponds with a location of the camera of the mobile device 387 when the housing 250 is clipped onto the mobile device 387.

Still referring to FIG. 8, as further shown, the housing 250 may include an optical lens 388. In some embodiments, the optical lens 388 is a long pass filter that attenuates the light generated by the LEDs 373 to 378 at wavelengths below 550 nm, and transmits longer wavelengths above 550 nm, thereby eliminating ambient lighting. According to one or more embodiments, the optical lens 388 is disposed at a location that corresponds with a location of the camera of the mobile device 387 when the housing 250 is clipped onto the mobile device 387.

Figure 9:
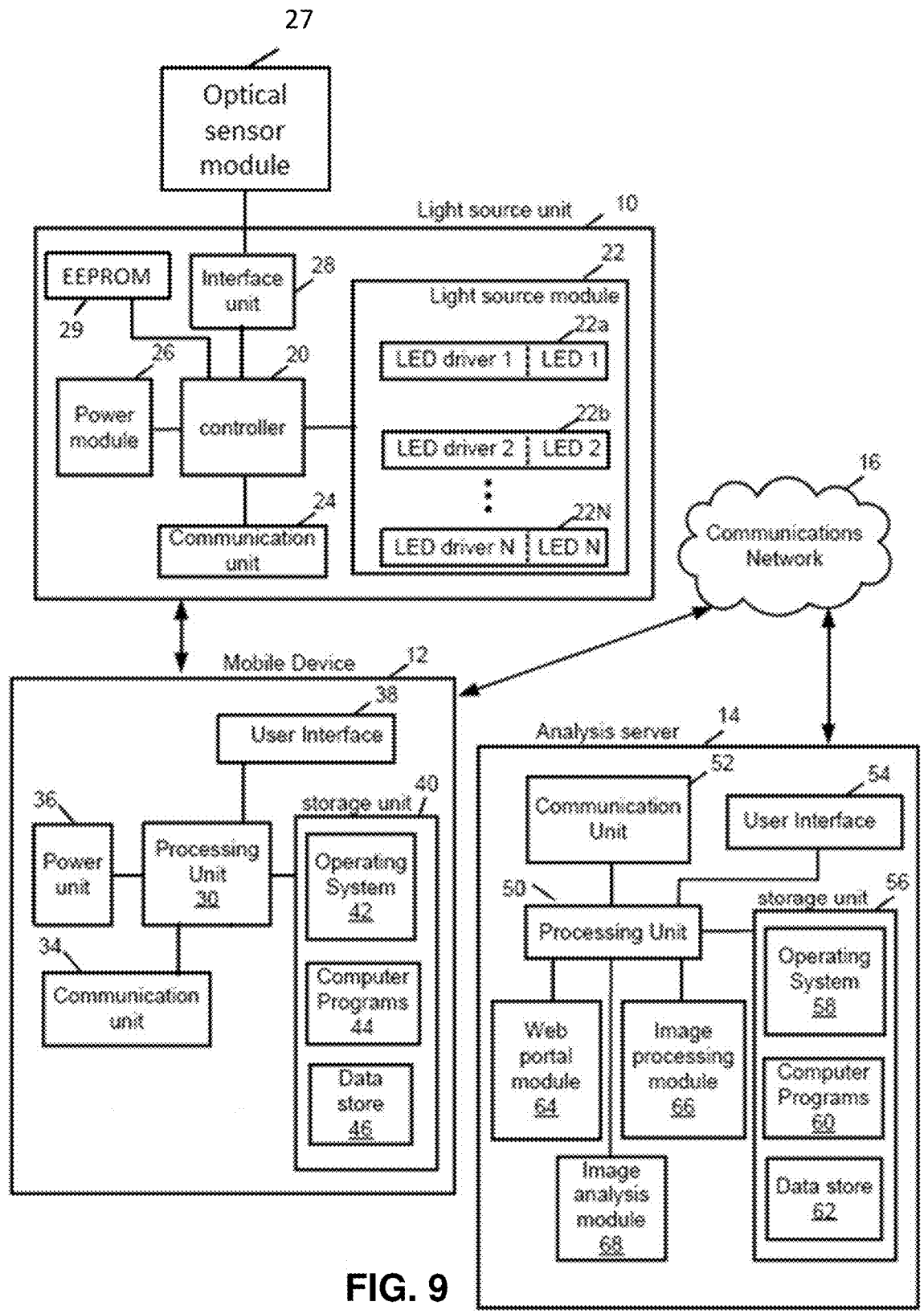
FIG. 9 is a block diagram of an example embodiment of a system including a light source unit, an optical sensor module, and a mobile device for remote tissue assessment.

Referring now to FIG. 9, a block diagram of an example embodiment of a system including a light source unit 10, an optical sensor module 27, and a mobile device 12 for remote tissue assessment is shown. As shown, FIG. 9 includes some reference numerals that are the same as those shown in FIG. 1, as previously described. The same reference numerals in FIGS. 1 and 9 refer to the same components of the system, as previously described with respect to FIG. 1. Accordingly, descriptions of the same reference numerals will not be repeated here. That is, unless necessary for understanding, only the differences between the embodiments shown in FIGS. 1 and 9 will be described with respect to FIG. 9.

As shown in FIG. 9, in some embodiments, an off-board optical sensor module 27 replaces the function of the camera 32 of the mobile device 12, as shown in FIG. 1. The optical sensor module 27 is a digital camera including an optical sensor and a lens. According to one or more embodiments, the optical sensor is a charged-couple device (CCD) or a complementary metal oxide semiconductor (CMOS) sensor. As shown in FIG. 9, the optical sensor module 27 is in communication with the light source unit 10 via the interface unit 28. For example, the interface unit 28 may include a USB interface to allow the off-board optical sensor module 27 to electrically connect to the light source unit 10.

In this example embodiment, the LEDs 22a to 22N surround the optical sensor module 27, where N is the number of chromophores to be solved. According to one or more embodiments, N=6. In this way, light generated by the LEDs 1 to N may be received by the optical sensor module 27 and focused via the lens onto the optical sensor. As previously described, the light generated may have a discrete wavelength corresponding to the physiological marker to be measured. In some embodiments, the optical sensor of the optical sensor module 27 includes a long pass filter that attenuates the light generated by the LEDs 1 to N at wavelengths below 500 nm, and transmits longer wavelengths above 500 nm. Also, in some embodiments, the optical sensor module 27 via the lens and the optical sensor may be able to focus light on a plane approximately 30 cm away.

In this embodiment, the power module 26 of the light source unit 10 includes a voltage regulator that may be coupled to a lithium polymer battery that is used to provide enough current to flow to the LEDs 22a to 22N (e.g., 2 A peak power), as previously described.

Still referring to FIG. 9, the interface unit 28 of the light source unit 10 is connected to the controller 20. In this way, the off-board optical sensor module 27 may be in communication with the controller 20 via the interface unit 28. Further, the controller 20 is connected to the light source module 22, which includes LEDs 1 to N. Accordingly, in one or more embodiments, the controller 20 may control the optical sensor module 27 to execute a focus and capture command when light generated by the surrounding LEDs 1 to N illuminates the tissue region. More specifically, the controller 20 may control the exposure time and/or the sensor sensitivity of the optical sensor module 27. As a result, the optical sensor module 27 may obtain precisely controlled and focused image data as instructed by the controller 20.

In this way, the optical sensor module 27 may sequentially obtain M image datasets of the tissue region (for M physiological markers actually used, where M is an integer less than or equal to the N LEDs) when the tissue region is illuminated by the light signal having a discrete wavelength selected from M discrete unique frequencies, as previously described. Further, the optical sensor module 27 may obtain a reference image dataset of the tissue region when the tissue region is not illuminated, as previously described. Thus, the optical sensor module 27 obtains M image datasets of the tissue region with illumination, and one reference image dataset of the tissue region without illumination for a total of M+1 image datasets.

Still referring to FIG. 9, the light source unit 10 includes an EEPROM chip 29 connected to the controller 20. In one or more embodiments, image datasets obtained by the off-board optical sensor module 27 may be stored on the EEPROM chip 29 via the interface unit 28 and the controller 20. Moreover, image datasets stored on the EEPROM chip 29 may be retrieved at the instruction of the controller 20 and passed to the communication unit 24 of the light source unit 10. As previously described, the controller 20 of the light source unit 10 may use the communication unit 24 to communicate with the communication unit 34 of the mobile device 12 via a direct wireless connection. In one or more embodiments, this wireless connection may be over WiFi or Bluetooth, as previously described. In this way, image datasets obtained by the optical sensor module 27 and stored on the EEPROM chip 29 may be transmitted from the light source unit 10 to the mobile device 12.

Still referring to FIG. 9, the mobile device 12 includes computer programs 44 stored in the storage unit 40. In one or more embodiments, the computer programs 44 may include an application for tissue assessment of a tissue region running on the operating system 42. The application coupled with the processing unit 30 of the mobile device 12 may perform the image processing and image analysis of the image datasets according to one or more embodiments. In other embodiments, the mobile device 12 may transmit the image datasets to the analysis server 14 via the communications network 16 for processing and analysis, as previously described.

In view of the embodiments described herein, Multispectral Mobile Tissue Assessment (MIMOSA) is a hand held device that attaches to a user's mobile device, and that includes a light source unit having a set of specialized LEDs that illuminate the skin with non-visible (near-infrared) light. Advantageously, near-infrared light illuminates the deep part of the tissue with light at specific wavelengths that can provide information about whether the tissue is healthy or not. In some embodiments, it is as simple as pressing the camera button on the mobile device. In other embodiments, it is as simple as pressing the camera button on the off-board digital camera or optical sensor module.

Advantageously, the MIMOSA hardware is also connected to a software platform that enables remote monitoring of patients from home. Through this service (called eMIMO), the client remains connected to their healthcare provider, who is notified automatically if the patient needs to be seen in person. Remote monitoring saves the healthcare system the significant costs associated with routine hospital or doctors' visits, without sacrificing patient care.

A diabetic patient is the end user of the product MIMOSA and service eMIMO. Diabetic care was revolutionized when diabetic patients started using glucometers to monitor their blood sugars at home. However, there are currently no tools to assess the health of the diabetic lower extremity, despite the significant morbidity and mortality associated with diabetic foot ulcers (DFUs). MIMOSA allows the patient to take a picture of their foot to determine if they are at risk for a DFU. Currently, this assessment is performed in a hospital environment by highly specialized health care providers. This assessment by a highly specialized team is expensive for the health care system and also not available to patients in remote locations. MIMOSA allows the patient to perform a daily measurement of their foot health, pre-warns the patient that there is a pending problem, and alerts their health care provider that the patient needs a clinical visit to perform more specific tests.

With respect to the end user (e.g., diabetic patient), MIMOSA is an early warning tool of impending tissue injury. It may prevent patients from having their legs amputated. The one year mortality risk after an amputation is 30%, which is greater than the risk of dying from breast or colon cancer. MIMOSA reduces the number of clinic visits by a factor of 2-4. In patients not located close to specialized wound centers, monitoring does not occur regularly and increases the risk of amputation 2-3 fold. Therefore, MIMOSA also has the potential to increase equity in health care provision for all patients with diabetes.

With respect to the hospital or care provider, MIMOSA may result in reduced visits to the hospital, reduced costs in treating wounds and amputations, earlier interventions, and cost-effective treatments for the care of diabetic foot ulcers.

With respect to the wound market industry, MIMOSA is a tissue physiology monitoring device that permits direct feedback for the effectiveness of wound treatments. This will permit further refinement of current products and the development of new and cost effective treatments for wound care. In addition, industry could provide clients with physiology images for marketing and sale of their current wound care products. For example, product X performs best in situation A as shown by the MIMOSA images, giving real time feedback for the wound treatment modality.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

What is claimed is:

1. A method for performing remote tissue assessment of a tissue region, wherein the method comprises:
    selecting imaging parameters for determining M physiological markers of interest for the tissue region, where the imaging parameters include M discrete unique wavelengths being selected to measure the M physiological markers of interest and to minimize a condition number of an inversion matrix selected based on absorption coefficients of the M physiological markers;
    obtaining M image datasets of the tissue region based on a reflectance of the tissue region when the tissue region is illuminated by a light signal having a unique discrete wavelength selected from the M discrete unique wavelengths;
    obtaining a reference image dataset of the tissue region when the tissue region is not illuminated;
    performing image subtraction between the M image datasets and the reference image dataset to obtain M reflectance datasets;
    processing the M reflectance datasets to obtain M marker maps where each marker map corresponds to a different physiological marker, wherein processing the M reflectance datasets comprises determining a reflectance contribution of each of the physiological markers of interest;
    and analyzing at least one of the marker maps to determine whether a physiological condition exists at the tissue region or to monitor the status of an existing physiological condition at the tissue region.

2. The method of claim 1, wherein the method further comprises providing a recommendation depending on the analysis results, the recommendation comprising one of performing further assessment of the tissue region and applying a type of treatment to the tissue region.

3. The method of claim 1, wherein the discrete wavelengths are selected in the range of about 600 nm to 1,000 nm.

4. The method of claim 3, wherein the discrete wavelengths comprise 620, 630, 700, 810, 880 and 940 nm.

5. The method of claim 1, wherein the analysis comprises combining at least two of the marker maps to create a combined marker map and performing measurements on the combined marker map.

6. The method of claim 1, further comprising one or more of the following characteristics:
    (a) the physiological markers for the marker maps comprise at least one of total hemoglobin, oxygen saturation, methemoglobin, water, and melanin;
    (b) the marker map comprises a water marker map that is used for at least one of determining end points of resuscitation, monitoring burn edema, monitoring sepsis and monitoring infection:
    (c) the marker map comprises a collagen marker map that is used to monitor at least one of wound healing, scar outcome and scar progression;
    (d) the marker map comprises a melanin marker map that is used to monitor at least one of progression and regression of melanin deposition in skin, scar, and surrounding tissue;
    (e) generating an alert when the analysis of the at least one marker map indicates a sudden change in the physiological condition;
    (f) determining a relationship between at least two of the marker map; and analyzing the determined relationship to determine the composition of blood oxygenation and oxidation for the tissue region; and/or
    (g) the processing comprises performing multispectral unmixing to generate the marker maps.

7. The method of claim 1, wherein the processing comprises performing multispectral unmixing to generate the marker maps and applying at least one of light distribution correction, non-intensity based image registration, image subtraction, image denoising and output denoising to improve the signal to noise ratio of the generated marker maps.

8. The method of claim 1, wherein the method comprises using a handheld portable imaging device for imaging the tissue region, the handheld portable imaging device including a light source unit for generating the light signal to illuminate the tissue region and a mobile device having a camera for obtaining the image datasets.

9. The method of claim 8, wherein the image datasets are sent from the mobile device to an analysis server which performs the processing and analysis of the image datasets.

10. The method of claim 8, wherein the mobile device performs the processing and analysis of the image datasets.

11. The method of claim 1, wherein the physiological markers for the marker maps comprise methemoglobin.

12. The method of claim 1, wherein the method comprises using a system for imaging the tissue region, the system comprising: a light source unit for generating the light signal to illuminate the tissue region; an optical sensor module for obtaining the image datasets, wherein the optical sensor module is in communication with the light source unit; and a mobile device in communication with the light source unit.

13. The method of claim 12, wherein the image datasets are sent from the optical sensor module to the mobile device using a communication unit of the light source unit, and wherein: (a) the mobile device performs the processing and analysis of the image datasets; or (b) the image datasets are subsequently sent from the mobile device to an analysis server, which performs the processing and analysis of the image datasets.

14. The method of claim 12, wherein obtaining the image datasets comprises controlling the optical sensor module to execute a focus and capture command.

15. The method of claim 14, wherein obtaining the image datasets further comprises controlling at least one of exposure time and sensor sensitivity of the optical sensor module.

16. The method of claim 1, wherein analyzing the at least one of the marker maps comprises performing measurements on the at least one of the marker maps and comparing the measurements to a threshold determined based on the at least one marker map analyzed and wherein the method further comprises:
  in response to determining that the physiological condition exists at the tissue region or in response to identifying a change in the status of the existing physiological condition at the tissue region, generating an alert.

17. A system for remote tissue assessment of a tissue region, wherein the system comprises:
  a light source unit for generating a light signal to illuminate the tissue region, the light signal having a unique discrete wavelength selected from M discrete unique wavelengths; and
  a mobile device having a camera for obtaining M image datasets of the tissue region based on a reflectance of the tissue region when the tissue region is illuminated by the light signal and obtaining a reference image dataset of the tissue region when the tissue region is not illuminated,
  wherein the system is configured to:
    select imaging parameters for determining the M physiological markers of interest for the tissue region, the M discrete unique wavelengths being selected to measure M physiological markers of interest and to minimize a condition number of an inversion matrix selected based on absorption coefficients of the M physiological markers;
    perform image subtraction between the M image datasets the reference image dataset to obtain M reflectance datasets;
    process the M reflectance datasets to obtain M marker maps where each marker map corresponds to a different physiological marker, wherein processing the M reflectance datasets comprises determining a reflectance contribution of each of the physiological markers of interest; and
    analyze at least one of the marker maps to determine whether a physiological condition exists at the tissue region or to monitor the status of an existing physiological condition at the tissue region.

18. The system of claim 17, wherein the system further comprises an analysis server portal.

19. The system of claim 17, wherein the system is configured for providing a recommendation depending on the analysis results, the recommendation comprising one of performing further assessment of the tissue region and applying a type of treatment to the tissue region.

20. The system of claim 17, wherein analyzing the at least one of the marker maps comprises performing measurements on the at least one of the marker maps and comparing the measurements to a threshold determined based on the at least one marker map analyzed and wherein the system is further configured to:
  in response to the determining that the physiological condition exists at the tissue region or in response to identifying a change in the status of the existing physiological condition at the tissue region, generate an alert.

21. A system for remote tissue assessment of a tissue region, wherein the system comprises:
  a light source unit for generating a light signal to illuminate the tissue region, the light signal having a discrete wavelength selected from M discrete unique wavelengths;
  an optical sensor module for obtaining M image datasets of the tissue region based on a reflectance of the tissue region when the tissue region is illuminated by the light signal and obtaining a reference image dataset of the tissue region when the tissue region is not illuminated, wherein the optical sensor module is in communication with the light source unit; and
  a mobile device in communication with the light source unit,
  wherein the system is configured to:
    select imaging parameters for determining the M physiological markers of interest for the tissue region, the imaging parameters including the M discrete unique wavelengths that are selected to measure M physiological markers of interest and to minimize a condition number of an inversion matrix selected based on absorption coefficients of the M physiological markers;
    perform image subtraction between the M image datasets the reference image dataset to obtain M reflectance datasets;
    process the M reflectance datasets to obtain M marker maps where each marker map corresponds to a different physiological marker, wherein processing the M reflectance datasets comprises determining a reflectance contribution of each of the physiological markers of interest; and
    analyze at least one of the marker maps to determine whether a physiological condition exists at the tissue region or to monitor the status of an existing physiological condition at the tissue region.

22. The system of claim 21, wherein the system further comprises an analysis server portal.

23. The system of claim 21, wherein the optical sensor module is in communication with the light source unit via a USB interface.

24. The system of claim 21, wherein at least one physiological marker for the marker maps is methemoglobin.

25. The system of claim 21, wherein analyzing the at least one of the marker maps comprises performing measurements on the at least one of the marker maps and comparing the measurements to a threshold determined based on the at least one marker map analyzed and wherein the system is further configured to:
  in response to the determining that the physiological condition exists at the tissue region or in response to identifying a change in the status of the existing physiological condition at the tissue region, generate an alert.

\* \* \* \* \*